(12) United States Patent
Young et al.

(10) Patent No.: US 9,650,414 B1
(45) Date of Patent: May 16, 2017

(54) DUAL-ACTION EP4 AGONIST—BISPHOSPHONATE CONJUGATES AND USES THEREOF

(71) Applicant: Simon Fraser University, Burnaby (CA)

(72) Inventors: Robert N. Young, Vancouver (CA); Gang Chen, Langley (CA); Haibo Xie, Coquitlam (CA)

(73) Assignee: Simon Fraser University, Burnaby (CA)

( * ) Notice: Subject to any disclaimer, the term of this patent is extended or adjusted under 35 U.S.C. 154(b) by 0 days.

(21) Appl. No.: 14/726,020

(22) Filed: May 29, 2015

Related U.S. Application Data

(60) Provisional application No. 62/005,778, filed on May 30, 2014.

(51) Int. Cl.
  *C07K 5/06* (2006.01)
  *C07K 5/062* (2006.01)
  *A61K 38/00* (2006.01)

(52) U.S. Cl.
  CPC .......... *C07K 5/06043* (2013.01); *A61K 38/00* (2013.01)

(58) Field of Classification Search
  CPC ..... C07K 5/06; A61K 38/00; A61K 47/48074
  USPC ......................................................... 514/19
  See application file for complete search history.

(56) References Cited

U.S. PATENT DOCUMENTS

| | | | |
|---|---|---|---|
| 4,320,136 A | 3/1982 | Scribner | |
| 4,922,007 A | 5/1990 | Kieczykowski et al. | |
| 5,019,651 A | 5/1991 | Kieczykowski | |
| 5,409,911 A | 4/1995 | Tyler et al. | |
| 5,510,517 A | 4/1996 | Dauer et al. | |
| 5,648,491 A | 7/1997 | Dauer et al. | |
| 6,121,253 A | 9/2000 | Han et al. | |
| 7,109,223 B2 | 9/2006 | Han et al. | |
| 7,238,710 B2 | 7/2007 | Billot et al. | |
| 2005/0239872 A1 | 10/2005 | Billot et al. | |
| 2006/0258726 A1 | 11/2006 | Billot et al. | |
| 2013/0157984 A1 | 6/2013 | Young et al. | |

FOREIGN PATENT DOCUMENTS

| | | |
|---|---|---|
| CA | 2648159 A1 | 10/2007 |
| EP | 0855389 A2 | 7/1998 |
| EP | 1114816 A1 | 7/2001 |
| EP | 1132086 A2 | 9/2001 |
| EP | 2576575 | 4/2013 |
| WO | WO-01/72268 A1 | 10/2001 |
| WO | WO-02/24647 A1 | 3/2002 |
| WO | WO-02/42268 A2 | 5/2002 |
| WO | WO-03/047417 A2 | 6/2003 |
| WO | WO-2005/116010 A1 | 12/2005 |
| WO | WO-2011/147034 A1 | 12/2011 |
| WO | WO-2016199111 A1 | 12/2016 |

OTHER PUBLICATIONS

Arns et al., "Design and synthesis of novel bone-targeting dual-action pro-drugs for the treatment and reversal of osteoporosis," Bioorg Med Chem. 20(6):2131-40 (2012).
Arns et al., "Asymmetric [3H]-labeling using ruthenium catalyzed transfer hydrogenation," J Labelled Comp Radiopharm. 53:205-7 (2010).
Arns et al., "Development of Dual Prodrug Conjugates for the Treatment of Osteoporosis," 93rd Canadian Chemistry Conference and Exhibition, 2010 (1 page).
Brümmer et al., "Antibody-catalyzed hydrolysis of oligomeric esters: a model for the degradation of polymeric materials," Chem Commun. 19-20 (2001).
Chen et al., "Determination of the Rat in Vivo Pharmacokinetic Profile of a Bone-Targeting Dual-Action Pro-Drug for Treatment of Osteoporosis," Bioconjug Chem. 26:1095-103 (2015).

(Continued)

*Primary Examiner* — David Lukton
(74) *Attorney, Agent, or Firm* — Clark & Elbing LLP

(57) ABSTRACT

The invention provides in part, compounds according to Formula I:

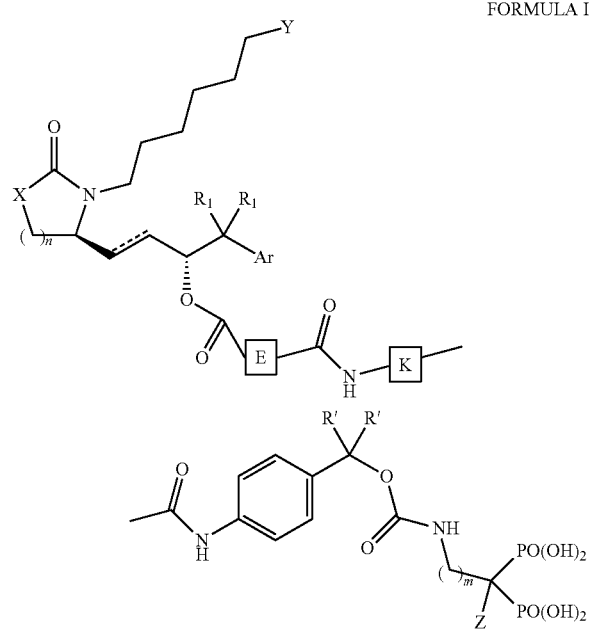

FORMULA I and uses thereof.

17 Claims, 8 Drawing Sheets

(56) References Cited

OTHER PUBLICATIONS

Gediya et al., "Design, synthesis, and evaluation of novel mutual prodrugs (hybrid drugs) of all-trans-retinoic acid and histone deacetylase inhibitors with enhanced anticancer activities in breast and prostate cancer cells in vitro," J Med Chem. 51(13):3895-904 (2008).
Hoyer, "Causes and consequences of disturbances of cerebral glucose metabolism in sporadic Alzheimer disease: therapeutic implications," Adv Exp Med Biol. 541:135-52 (2004).
Liu et al., "Effects of a New Anabolic Drug in Treating Postmenopausal Osteoporosis Using the Ovariectomized Rat Model," ASBMR 2013 Annual Meeting (2013).
Machwate et al., "Prostaglandin receptor EP(4) mediates the bone anabolic effects of PGE(2)," Mol Pharmacol. 60(1):36-41 (2001).

Esterase releases EP4 agonist then CatK releases BP

FORMULA 1

DUAL-ACTION EP4 AGONIST—BISPHOSPHONATE CONJUGATES AND USES THEREOF

FIELD OF INVENTION

The present invention relates to dual action EP4 agonist-bisphosphonate conjugate compounds.

BACKGROUND OF THE INVENTION

Prostaglandins are a sub-class of eicosanoids found in most body tissues and implicated in a variety of physiological functions in animals, including smooth muscle contraction, reproduction, autoimmunity, inflammation, reduction of intraocular pressure, etc. Prostaglandin $E_2$ ($PGE_2$) has been associated with various physiological and/or pathological conditions such as stimulation of bone formation, increase in bone mass, arthritis, pain, inflammation, cancer, multiple sclerosis, etc.

$PGE_2$ binds to four receptors (EP1, EP2, EP3 and EP4). The EP4 receptor is associated with intracellular cyclic adenosine monophosphate (cAMP) production, and is distributed in a wide variety of tissue types, suggesting a major role in PGE2-mediated biological events, such as smooth muscle relaxation, intraocular pressure, pain (in particular inflammatory, neuropathic and visceral pain), inflammation, neuroprotection, lymphocyte differentiation, bone metabolic processes, allergic activities, promotion of sleep, renal regulation, gastric or enteric mucus secretion and duodenal bicarbonate secretion. Prostaglandin $E_2$ has been implicated in the stimulation of bone growth through the EP4 receptor subtype (Machwate et al., Prostaglandin receptor $EP_4$ mediates the bone anabolic effects of $PGE_2$. *Molecular Pharmacology* 60, 36).

A variety of EP4 agonists have been described and include, without limitation, compounds as set forth in, for example, WO 02/24647, WO 02/42268, EP 1132086, EP 855389, EP 1114816, WO 01/46140, WO 01/72268. Many EP4 agonists have however been associated with systemic side effects.

Bisphosphonates are drugs used to strengthen bone as they have been implicated in inhibiting bone resorption and bone targeting (L. Gil et al., Prostaglandin $E_2$-bisphosphonate conjugates: potential agents for treatment of osteoporosis. *Bioorganic & Medicinal Chemistry* 7, 901).

Prostaglandin-bisphosphonate conjugate compounds are described in, for example, U.S. Pat. No. 5,409,911, U.S. Pat. No. 6,121,253 and WO 2011/147034.

Cathepsin-K (Cat-K) is an osteoclast protease (F. Lecaille et al., Selective inhibition of the collagenolytic activity of human cathepsin K by altering its S2 subsite specificity. *Biochemistry* 41, 8447).

SUMMARY OF THE INVENTION

The invention provides, in part, conjugate compounds in which a bone growth stimulating EP4 receptor agonist is conjugated to a bone targeting bisphosphonate via linking elements.

In one aspect, the invention provides a compound according to Formula I:

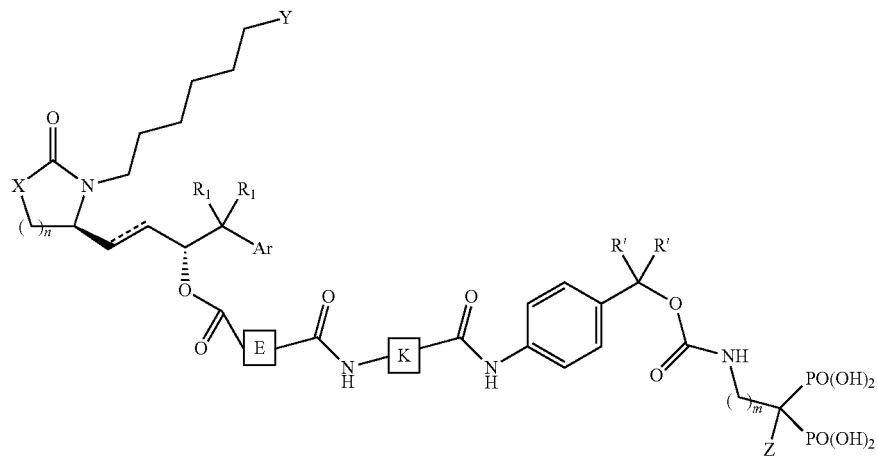

FORMULA I or a pharmaceutically acceptable salt thereof, where X is —$CH_2$—, —S—, —O—, or —NH—; Y is optionally substituted tetrazole, —C(O)OR', or —C(O)$NHSO_2$V; R' is H or lower alkyl; V is optionally substituted lower alkyl, optionally substituted aryl, or optionally substituted heteroalkyl; Z is H or OH; n is 1, 2 or 3; m is 0, 1, 2, 3, 4, 5, or 6; $R_1$ is each independently —H, halo, or lower alkyl; Ar is aryl or substituted aryl; E is an esterase-cleavable linker and K is a Cathepsin K (CatK)-cleavable peptide.

In alternative embodiments, the compound may be a compound according to Formula II:

FORMULA II

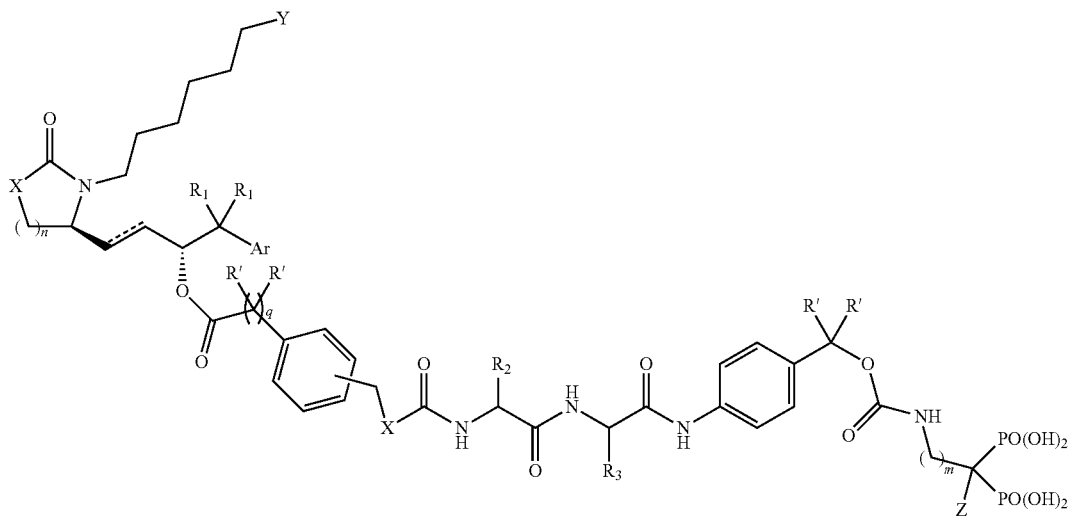

or a pharmaceutically acceptable salt thereof, where X is —CH$_2$—, —S—, —O—, or —NH—; Y is optionally substituted tetrazole, —C(O)OR', or —C(O)NHSO$_2$V; R' is H or lower alkyl; V is optionally substituted lower alkyl, optionally substituted aryl or optionally substituted heteroalkyl; Z is H or OH; n is 1, 2 or 3; m is 0, 1, 2, 3, 4, 5, or 6; q is 0, 1, 2 or 3; R$_1$ is each independently —H or halo, or lower alkyl; Ar is aryl or substituted aryl; and R$_2$ and R$_3$ are radicals selected from the radicals of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine or valine.

In some embodiments, R$_2$ may be CH$_2$CH$_2$CH$_2$C(=NH)NH$_2$.

In some embodiments, R$_3$ may be a lipophilic radical or may form a ring to the adjacent N. In some embodiments, R$_3$ may be CH$_2$CH(CH$_3$)CH$_3$, CH(CH$_3$)CH$_2$CH$_3$, or CH$_2$Ar.

In some embodiments, the compound may be (4-(((((4-((S)-2-((S)-2-(((((4-(2-(((R,E)-4-((R)-1-(7-ethoxy-7-oxoheptyl)-5-oxopyrrolidin-2-yl)-1,1-difluoro-1-phenylbut-3-en-2-yl)oxy)-2-oxoethyl)benzyl)oxy)carbonyl)amino)-4-methylpentanamido)-5-guanidinopentanamido)benzyl)oxy)carbonyl)amino)-1-hydroxybutane-1,1-diyl)bis(phosphonic acid) or (4-(((((4-((S)-2-((S)-2-(((((4-(2-(((R,E)-4-((R)-1-(7-ethoxy-7-oxoheptyl)-5-oxopyrrolidin-2-yl)-1,1-difluoro-1-(4-iodophenyl)but-3-en-2-yl)oxy)-2-oxoethyl)benzyl)oxy)carbonyl)amino)-4-methylpentanamido)-5-guanidinopentanamido)benzyl)oxy)carbonyl)amino)-1-hydroxybutane-1,1-diyl)bis(phosphonic acid).

The compound may be provided as a composition (e.g., a pharmaceutical composition) in combination with a carrier (e.g., a pharmaceutically acceptable carrier).

In alternative aspects, the invention provides a method of selectively delivering a compound to a bone or an associated site, by administering an effective amount of a compound according to the invention or a pharmaceutically acceptable salt thereof to a subject in need thereof. The bone may be a bone in need of treatment. The associated site may be a site adjacent to the bone in need of treatment.

In some embodiments, the bone, such as a bone in need of treatment, may be a green stick fracture, a compound fracture, a lateral fracture, a pathologic fracture resulting from an invasive tumor, a compression fracture, or a fracture requiring a surgical procedure for realignment of a bone.

In alternative aspects, the invention provides a method of treating or preventing a condition associated with abnormal or excessive bone loss, or with abnormal or reduced bone resorption, or with abnormal calcium metabolism by administering an effective amount of a compound according to the invention or a pharmaceutically acceptable salt thereof to a subject in need thereof.

In some embodiments, the condition may be osteoporosis (such as glucocorticoid-induced osteoporosis), Paget's disease, abnormally increased bone turnover, bone graft, periodontal disease, alveolar bone loss, tooth loss, bone fracture, periprostheticosteolysis, osteogenesis imperfecta, or metastatic bone disease.

In some embodiments, the subject may be a human.

This summary of the invention does not necessarily describe all features of the invention.

BRIEF DESCRIPTION OF THE FIGURES

These and other features of the invention will become more apparent from the following description in which reference is made to the appended tables wherein.

DETAILED DESCRIPTION

The present disclosure provides, in part, a dual-action EP4 agonist-bisphosphonate conjugate compound or "conjugate compound" and uses thereof.

Dual-Action Conjugate Compounds

Figure 1:
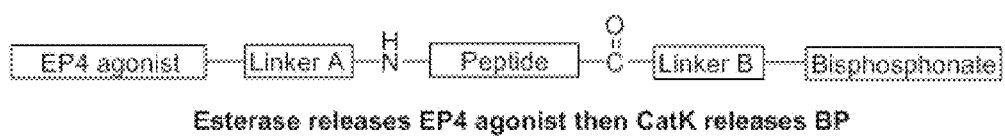
FIG. 1 is a schematic representation of a dual-action EP4 agonist-bisphosphonate conjugate compound.

A conjugate compound may include an EP4 agonist linked to the N-terminus of a peptide via an esterase-cleavable linker (Linker A); the C-terminus of the peptide may be linked via a Cathepsin K (CatK)-cleavable linker (Linker B) to a bisphosphonate (FIG. 1). Without being bound to any particular hypothesis, upon introduction into the bloodstream of an individual, the conjugate compound may travel throughout the body and attach itself to the bones by virtue of the avidity of the bisphosphonate for the bone mineral hydroxyapatite. Once attached, esterase enzymes may hydrolyze the ester bond so as to slowly release the EP4 agonist in situ to stimulate bone growth (and mitigate the side effects that are seen when the EP4 agonist is administered on its own). The action of CatK (which is involved in the process of bone resorption) may liberate the remainder of the conjugate compound including the bisphosphonate that is still attached to the bone surface.

Figure 2:
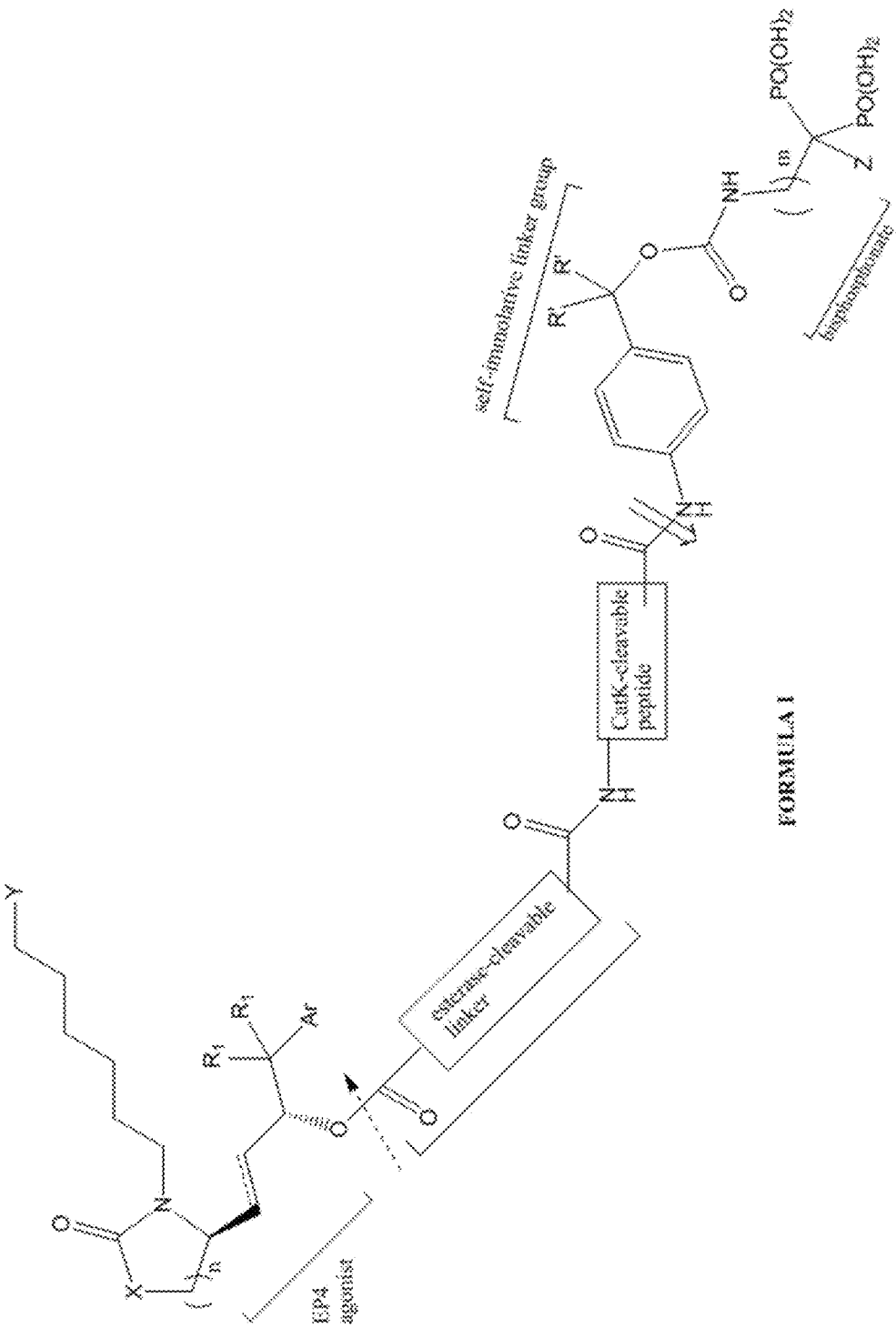
FIG. 2 is a representation of a dual-action EP4 agonist-bisphosphonate conjugate compound, designated Formula I, in which an EP4 agonist is attached to an esterase cleavable linker, which is then bonded to the N-terminal end of a peptide and where the C-terminus of the peptide is bonded to a bisphosphonate.

In some embodiments, a conjugate compound may be as shown in Formula I, in which an EP4 agonist is attached via an ester bond to an esterase cleavable linker, which is then bonded to the N-terminal end of a peptide (for example, via a methylenoxycarbonyl group) and where the C-terminus of the peptide (the CatK cleavage site) is bonded to an aminophenylmethylenoxycarbonyl group to the NH of an aminobisphosphonate (FIG. 2). In this embodiment, the EP4 agonist may be released by esterases and the bisphosphonate may be released by the action of Cathepsin K.

The structure of Formula I may be represented as follows, where

X may be —$CH_2$—, —S—, —O—, or —NH—;

Y may be optionally substituted tetrazole, —C(O)OR', or —C(O)NHSO$_2$V;

R' may be H or lower alkyl;

V may be optionally substituted lower alkyl, optionally substituted aryl, or optionally substituted heteroalkyl;

Z may be H or OH;

n may be 1, 2 or 3;

m may be 0, 1, 2, 3, 4, 5, or 6;

$R_1$ may each independently be —H, halo, or lower alkyl;

Ar may be aryl or substituted aryl;

E may be an esterase-cleavable linker and

K may be a CatK-cleavable peptide.

The CatK-cleavable peptide may include two or more of the 20 natural amino acids: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine or valine, or any combination thereof. In alternative embodiments, CatK-cleavable peptides may be selected from peptides including two or more of arginine, phenylalanine, leucine, isoleucine or proline, or various combinations of these amino acids, which may be generated as described herein or known in the art.

Esterase-cleavable linkers may be selected as described herein or known in the art.

Figure 3:
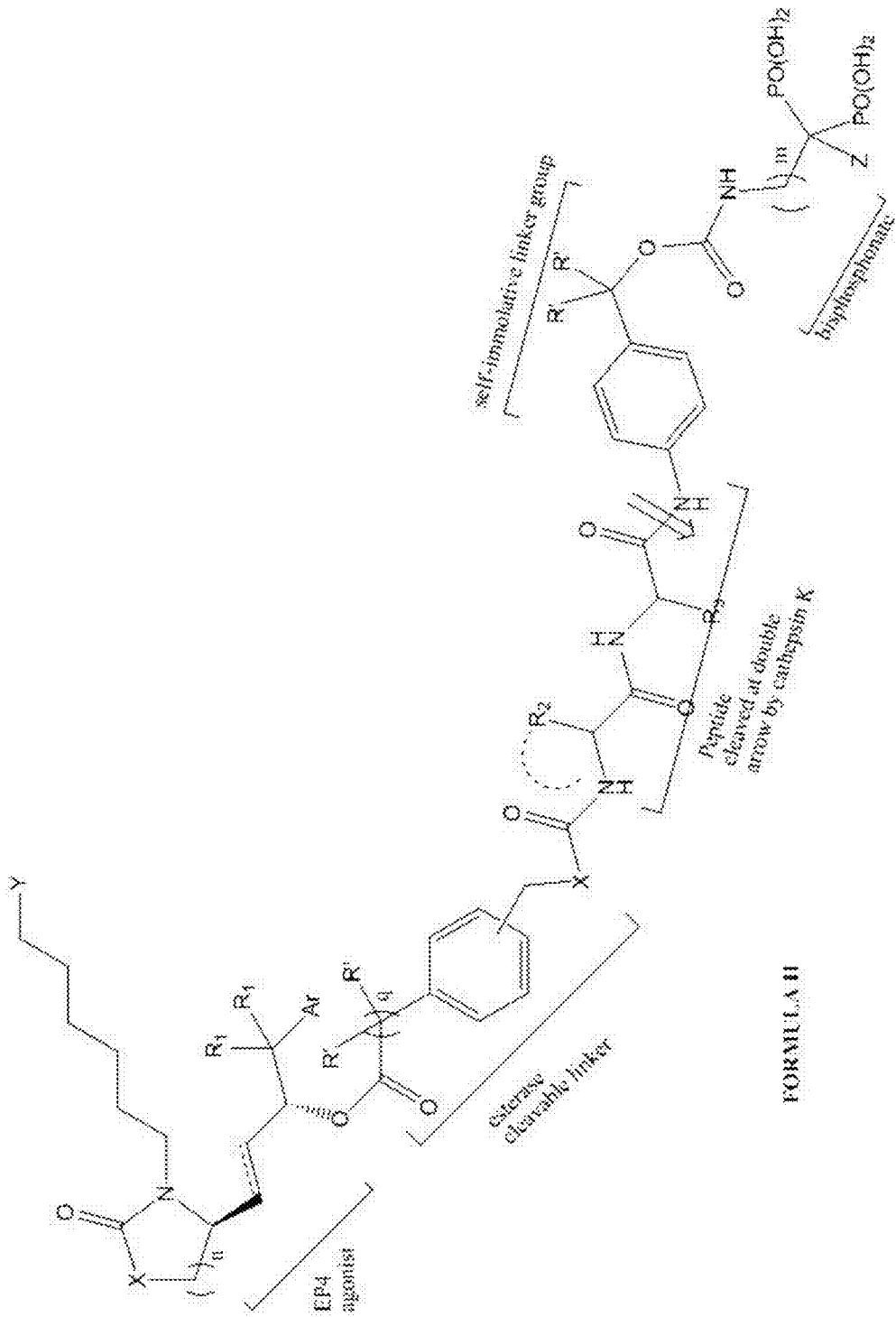
FIG. 3 is a representation of a dual-action EP4 agonist-bisphosphonate conjugate compound, designated Formula II, in which an EP4 agonist attached via an ester bond to a phenylacetic acid moiety, which is then bonded to the N-terminal end of a peptide (for example, via a methylenoxycarbonyl group) and where the C-terminus of the peptide (the CatK cleavage site) is bonded to an aminophenylmethyenoxycarbonyl group to the NH of the aminobisphosphonate.

In alternative embodiments, a conjugate compound may be as shown in Formula II, in which an EP4 agonist attached via an ester bond to a phenylacetic acid moiety, which is then bonded to the N-terminal end of the peptide (for example, via a methylenoxycarbonyl group) and where the C-terminus of the peptide (the cleavage site) is bonded to an aminophenylmethyenoxycabonyl group to the NH of the aminobisphosphonate (FIG. 3). In this embodiment, the EP4 agonist may be released by esterases and the bisphosphonate may be released by the action of Cathepsin K.

The structure of Formula II may be represented as follows,

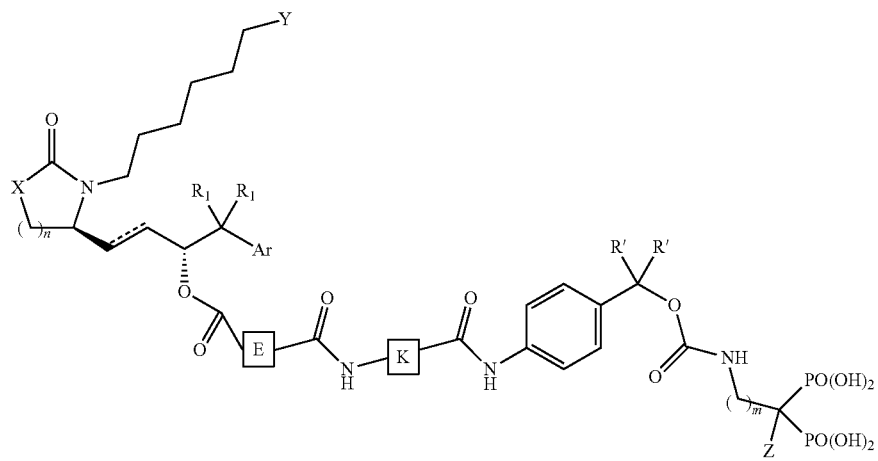

FORMULA I

FORMULA II

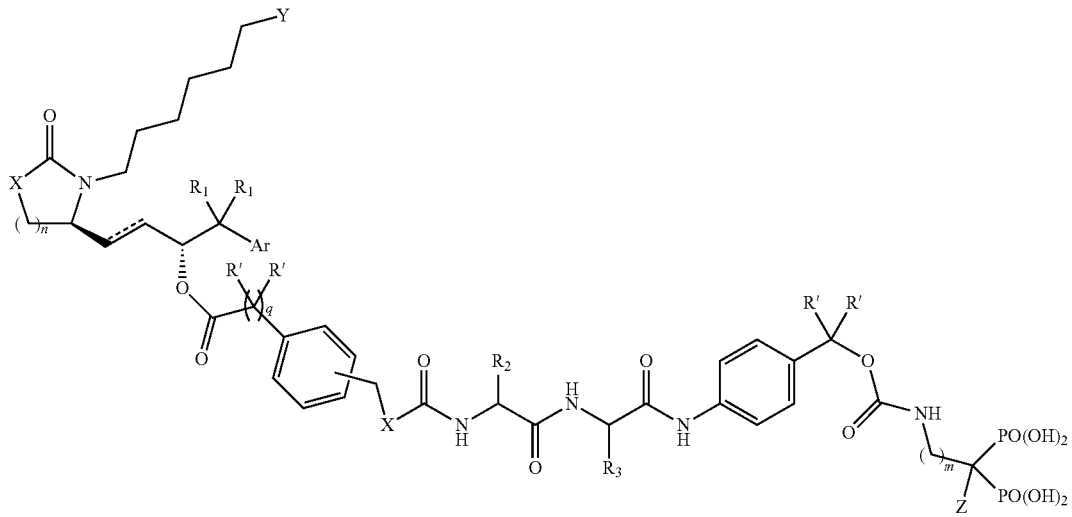

where
- X may be —CH$_2$—, —S—, —O—, or —NH—;
- Y may be optionally substituted tetrazole, —C(O)OR', or —C(O)NHSO$_2$V;
- R' may be H or lower alkyl;
- V may be optionally substituted lower alkyl, optionally substituted aryl or optionally substituted heteroalkyl;
- Z may be H or OH;
- n may be 1, 2 or 3;
- m may be 0, 1, 2, 3, 4, 5, or 6;
- q may be 0, 1, 2 or 3;
- R$_1$ may each independently be —H or halo, or lower alkyl;
- Ar may be aryl or substituted aryl; and
- R$_2$ and R$_3$ may independently be radicals chosen from the 20 natural amino acids, such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine or valine.

In some embodiments, R$_2$ may be CH$_2$CH$_2$CH$_2$C(=NH)NH$_2$.

In some embodiments, R$_3$ may be a lipophilic radical, such as CH$_2$CH(CH$_3$)CH$_3$, or CH(CH$_3$)CH$_2$CH$_3$, or CH$_2$Aryl, or may form a ring to the adjacent N (for example, proline).

In these embodiments, and without being bound to any particular hypothesis, upon introduction into the bloodstream of an individual, the conjugate compound may travel throughout the body and attach itself to the bones by virtue of the avidity of the bisphosphonate for the bone mineral hydroxyapatite. Once attached, esterase enzymes may hydrolyze the ester bond so as to slowly release the EP4 agonist in situ to stimulate bone growth (and mitigating the side effects that are seen when the agonist is administered on its own). Also, the action of CatK may cleave the N-terminal amide bond, liberating the aminophenyl-4-methylenoxycarbonylaminobisphosphonate that is still attached to the bone surface. This liberated moiety may spontaneously self-immolate to liberate the free aminobisphosphonate (still attached to bone) wherein it may exert its biological activity as an inhibitor of bone resorption. It is to be understood that while FIG. 3 depicts dipeptides such as leucine-arginine or proline-arginine, other peptides substrates, such as di-, tri- or tetra peptides substrates, which may be generated as described herein or known in the art, may also be used as linker peptides.

In alternative embodiments, the conjugate compounds may be substantially inactive until the action of Cathepsin K and/or esterases to release the EP4 agonist and bisphosphonate components as, for example, described herein.

By "substantially inactive" is meant less than 10-fold as active as compared to the free species (i.e., free EP agonist and free bisphosphonate).

By "release" as used herein is meant the liberation of an EP4 agonist moiety and a bisphosphonate moiety, for example, by hydrolyzation or enzyme action, from a conjugate compound as described herein. In alternative embodiments, at least about 5% to about 100%, for example, about 5%, 10%, 15%, 20%, 25%, 30%, 35%, 40%, 45%, 50%, 55%, 60%, 65%, 70%, 75%, 80%, 85%, 90%, 95%, or 100% or any value there between, of the EP4 agonist moiety and/or the bisphosphonate moiety is released in a suitable period of time. In alternative embodiments, the release may take a period of time, for example, about 1 day to about 30 days, or any value or set of values between this range, for example, about 7 days to about 14 days, such as about 7, 8, 9, 10, 11, 12, 13, or 14 days.

The conjugate compounds may provide either simultaneous or sequential delivery of the EP4 agonist and the bisphosphonate to a site of action, such as bone.

In some embodiments, the conjugate compounds may be delivered directly to bone.

In some embodiments, the conjugate compounds may be delivered directly to a site after pre-binding to a bone powder or bone graft material.

In some embodiments, the conjugate compounds may be substantially inactive prior to binding to bone.

In some embodiments, the conjugate compounds may reduce the systemic side effects associated with EP4 agonists.

In alternative embodiments, the conjugate compounds may be administered at lower doses compared to each of the free species (i.e., free EP agonist and free bisphosphonate).

In alternative embodiments, the conjugate compounds combine bone growth stimulating EP4 receptor selective agonists and bone resorption inhibiting amino-bisphosphonates in bone targeting pro-drugs which, on systemic administration, bind to bone and enzymatically liberate the two components in situ slowly over time thus avoiding the systemic side effects associated with EP4 agonists. The two actions may be additive or synergistic.

By "esterase cleavable linker" is meant a linking element that is cleaved by an esterase enzyme. Any suitable esterase cleavable linker, as known in the art or described herein, may be used. In some embodiments, a suitable esterase cleavable linker includes a phenylacetic acid moiety.

By "peptide that is a substrate for CatK" or "CatK-cleavable peptide" is meant a peptide that is, or has been shown to be, cleaved at the C terminus by Cathepsin K. Any suitable peptide that is a substrate for CatK, as known in the art or described herein, may be used. In some embodiments, CatK-cleavable peptide linkers may be chosen from the 20 natural amino acids. In alternative embodiments, CatK-cleavable peptide linkers may be selected from one or more of proline, leucine, argenine, glycine, or various combinations of these amino acids, such as Leucine-arginine or proline-arginine and other di-, tri- or tetra peptides substrates, that may be generated as described herein or known in the art.

By "self-immolative linker" is meant a linking element that, when liberated after cleavage by an enzyme such as Cathepsin K, spontaneously decomposes to liberate the other constituent bound at the other end of the linker element.

EP4 agonists include, without limitation, compounds containing a carboxyl or tetrazole group or an alcohol group, as set forth in, for example, WO 02/24647, WO 02/42268, EP 1132086, EP 855389, EP 1114816, WO 01/46140, WO 01/72268, etc. In some embodiments, EP4 agonists having a hydroxyl group at position 15 may be linked with an amino bisphosphonate via esterase cleavable linkers and/or cathepsin cleavable peptide linkers, as described herein.

By "bisphosphonate" as used herein is meant an amino-bisphosphonate compound. Any known bisphosphonate which has an secondary or primary amine functionality capable of coupling to linkers attached to EP4 agonists and which targets in vivo to bone may be used, whether or not that particular bisphosphonate has bone resorption inhibiting activity or is useful in the treatment of a disorder as described herein.

In some embodiments, bisphosphonates may have the following general structure,

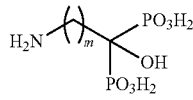

where m may be 1, 2, 3, 4, 5 or 6.

A "bisphosphonate moiety" as used herein is the portion of a bisphosphonate that is conjugated via the amino group to another compound, such as a self-immolative linker group, as described herein.

Bisphosphonates include, without limitation, alendronic acid, 4-amino-1-hydroxybutylidene-1, 1-bisphosphonic acid; alendronate (also known as alendronate sodium or alendronate monosodium trihydrate), 4-amino-1-hydroxybutylidene-1, 1-bisphosphonic acid monosodium trihydrate; alendronic acid and alendronate are described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997; 6-amino-1-hydroxyhexylidene-1, 1-bisphosphonic acid (neridronate); 3-amino-1-hydroxypropylidene-1, 1-bisphosphonic acid (pamidronate); or pharmaceutically acceptable salts thereof, or mixtures thereof.

Examples of EP4 agonists include compounds 1 and 2, or as described herein or known in the art, and examples of clinically active bisphosphonates (BPs) include alendronate/alendronic acid (3), pamidronate (4) or neridronate (5), or as described herein or known in the art.

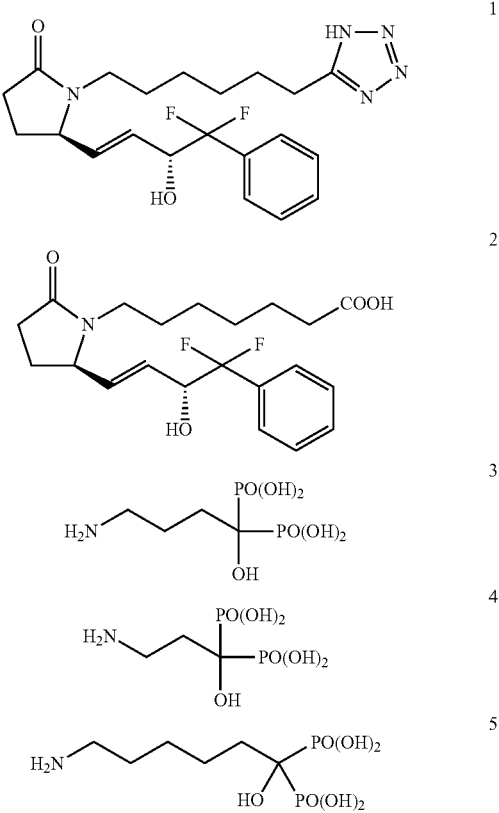

"Lower alkyl" as used herein refers to a straight or branched hydrocarbon chain group consisting solely of carbon and hydrogen atoms, containing no unsaturation and including, for example, from one to ten carbon atoms, or any value in between, and which is attached to the rest of the molecule by a single bond. Unless stated otherwise specifically in the specification, the alkyl group may be optionally substituted by one or more substituents as described herein. Unless stated otherwise specifically herein, it is understood that the substitution can occur on any carbon of the alkyl group. Examples of straight or branched chain alkyl groups include, but are not limited to, methyl, trifluoromethyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, 1-heptyl, or 1-octyl.

By a "ring structure" is meant a cycloalkyl, aryl, heteroaryl, or any cyclic structure that may be optionally substituted.

"Aryl" as used herein refers to a monocylic or bicyclic ring structure wherein all rings are aromatic and are formed of carbon atoms, for example, phenyl or naphthyl groups, including for example, 5-12 members. Unless stated otherwise specifically herein, the term "aryl" is meant to include aryl groups optionally substituted by one or more substituents as described herein.

Any group described herein may be substituted or unsubstituted. When substituted, a group may be substituted with any desired substituent or substituents such as one or more of the following group: H, alkyl ($C_{1-10}$), alkenyl ($C_{2-10}$), alkynyl ($C_{2-10}$), aryl (5-12 members), arylalkyl, arylalkenyl, or arylalkynyl, each of which may optionally contain one or more heteroatoms selected from O, S, P, N, F, Cl, Br, I, or B, and each of which may be further substituted, for example, by =O; or optionally substituted forms of acyl, arylacyl, alkyl-alkenyl-, alkynyl- or arylsulfonyl and forms thereof which contain heteroatoms in the alkyl, alkenyl, alkynyl or aryl moieties; halogen (e.g., chloro, iodo, bromo, or fluoro); hydroxyl; $C_{1-10}$ alkoxyl; amino (primary, secondary, or tertiary); nitro; thiol; thioether; imine; cyano; amido; carbamoyl; phosphonato; bisphosphonate; phosphine; carboxyl; thiocarbonyl; sulfonyl; sulfonamide; ketone; aldehyde; ester; oxo; haloalkyl (e.g., trifluoromethyl); cycloalkyl, which may be monocyclic or fused or non-fused polycyclic (e.g., cyclopropyl, cyclobutyl, cyclopentyl, or cyclohexyl), or non-aromatic heterocyclic, which may be monocyclic or fused or non-fused polycyclic (e.g., pyrrolidinyl, piperidinyl, piperazinyl, morpholinyl, or thiazinyl); and aromatic carbocyclic or heterocyclic, monocyclic or fused or non-fused polycyclic (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl). Specific substituent groups include benzyloxy; O-alkyl; O-aryl; aryl; aryl-lower alkyl, etc. A substituted group may have 1, 2, 3, 4, 5, 6, 7, 8, 9 or 10 substituent groups. These substituent groups may optionally be further substituted with a substituent as listed herein. Substituents may also be optionally substituted by a bridge structure, for example —OC(O)O— or —OC(O)NH—. In some embodiments, substituents are not further substituted.

"Optional" or "optionally" means that the subsequently described event of circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution. Examples of optionally substituted alkyl groups include, without limitation, methyl, ethyl, propyl, etc. Similarly, "optionally substituted tetrazole" means that the tetrazole group may or may not be substituted and the description includes both substituted tetrazoles and tetrazoles having no substitution.

Compounds may be in acid, base, or salt form.

Throughout this application, it is contemplated that the term "compound" or "compounds" refers to the compounds and conjugates discussed herein and includes precursors, intermediates, and derivatives of the compounds, including acyl-protected derivatives, and pharmaceutically acceptable salts of the compounds, precursors, and derivatives. The invention also includes prodrugs of the compounds, pharmaceutical compositions including the compounds and a pharmaceutically acceptable carrier, and pharmaceutical compositions including prodrugs of the compounds and a pharmaceutically acceptable carrier.

In some embodiments, all of the compounds of the invention contain at least one chiral center. In some embodiments, the compounds of the invention can have one or more chiral centers and/or double bonds. In some embodiments, the formulations, preparation, and compositions including compounds according to the invention can include mixtures of stereoisomers, individual stereoisomers, and enantiomeric mixtures, mixtures of multiple stereoisomers, double-bond isomers (i.e., geometric E/Z isomers) or diastereomers (e.g., enantiomers (i.e., (+) or (−)) or cis/trans isomers). In some embodiments, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. In general, the compound may be supplied in any desired degree of chiral purity.

Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

As used herein the singular forms "a", "and", and "the" include plural referents unless the context clearly dictates otherwise. For example, "a compound" refers to one or more of such compounds, and equivalents thereof as known to those skilled in the art.

EP4 agonist-bisphosphonate conjugates may be prepared as described herein or elsewhere. It is to be understood that the modifications of the methods and schemes as described herein, when performed using standard techniques or achieved by routine experimentations, are encompassed herein.

Therapeutic Indications

A variety of conditions or disorders in humans and other mammals involve or are associated with abnormal or excessive bone loss, or with abnormal or reduced bone resorption, or with abnormal calcium metabolism. Such conditions or disorders include, but are not limited to, osteoporosis, which may include low bone mass and microarchitectural deterioration of bone tissue, with a consequent increase in bone fragility and susceptibility to fracture, glucocorticoid-induced osteoporosis, Paget's disease, abnormally increased bone turnover, bone graft, periodontal disease, alveolar bone loss, tooth loss, bone fractures, periprosthetic osteolysis, osteogenesis imperfecta, metastatic bone disease, etc.

Accordingly, the conjugate compounds, as described herein, may be used to treat or prevent conditions or disorders associated with abnormal or excessive bone loss, or with abnormal or reduced bone resorption, or with abnormal calcium metabolism. It is to be understood that full treatment or prevention is not required and that partial treatment or prevention, relative to a suitable control, is contemplated.

In alternative embodiments, the invention provides methods of enhancing or elevating levels of bone stimulation or inhibiting bone resorption in animal subjects, such as, veterinary and human subjects. This elevation or inhibition can be useful for the prevention or treatment of conditions or disorders associated with abnormal or excessive bone loss, or with abnormal or reduced bone resorption, or with abnormal calcium metabolism. It is to be understood that full elevation or inhibition is not required and that the methods include partial elevation or inhibition relative to a suitable control.

The effectiveness of the compounds in prevention or treatment of conditions or disorders associated with abnormal or excessive bone loss, or with abnormal or reduced bone resorption, or with abnormal calcium metabolism may be confirmed by testing the ability of the compounds to enhance or elevate bone stimulation or inhibit bone resorption using standard techniques.

For example, the conjugate compounds may be evaluated first for in vitro for stability in plasma and then in normal animals (e.g., rats) for selective uptake into bones and slow release of the two components. When suitable conjugate(s) are identified, optimized compound(s) may be evaluated in animal models of osteoporosis or for example in an in vitro model of osteogenesis, i.e., neonatal rat calvaria cell cultures. Then the conjugate compounds may be used in for example in vivo or other assays to show efficacy and tolerability suitable for further development as novel therapies for treatment of disorders and conditions as described herein or found in the art.

In general, the methods of the invention are effected by administering a conjugate compound according to the invention to a subject in need thereof, or by contacting a cell or a sample with a conjugate compound according to the invention, for example, a pharmaceutical composition comprising a therapeutically effective amount of the compound according to any one or more of Formula I or II.

Pharmaceutical & Veterinary Compositions, Dosages, and Administration

Pharmaceutical compositions including the conjugate compounds according to the invention, or for use according to the invention, are contemplated as being within the scope of the invention. In some embodiments, pharmaceutical compositions including an effective amount of a conjugate compound according to any one or more of Formula I or II are provided.

In some embodiments, the conjugate compounds according to the invention target bone or a site at which bone growth stimulation or inhibition of bone resorption is required. Such a site includes both the area adjacent to a section of bone or group of bones in need of treatment in a subject in need thereof or a region inside the bone, including the site of a fracture or opening which occurs naturally or is intentionally made in the bone or group of bones. Bones in need of treatment include green stick fractures, compound fractures, lateral fractures, pathologic fractures resulting from invasive tumors, compression fractures and fractures that require surgical procedures for realignment of bones.

The conjugate compounds may, for example, be preabsorbed onto hydroxyapatite, synthetic bone matrix (such as monetite or brushite) or bone matrix and then this matrix implanted into sites in the body where bone growth is desired, such as to aid in and accelerate bone fusion in spine or joints or in jaw after tooth extraction. The conjugate compounds may also be administered locally onto bone sites (such as spine, jaw, joints) to locally enhance bone growth.

The conjugate compounds of Formula I or II, and their pharmaceutically acceptable salts, stereoisomers, solvates, and derivatives are useful because they have pharmacological activity in animals, including humans. In some embodiments, the conjugate compounds according to the invention are stable in plasma, when administered to a subject.

In some embodiments, conjugate compounds according to the invention, or for use according to the invention, may be provided in combination with any other active agents or pharmaceutical compositions where such combined therapy is useful to treat or prevent conditions or disorders associated with abnormal or excessive bone loss, or with abnormal or reduced bone resorption, or with abnormal calcium metabolism, for example, to treat any condition or disorder described herein.

In some embodiments, conjugate compounds according to the invention, or for use according to the invention, may be provided in combination with one or more agents useful in the prevention or treatment of conditions or disorders associated with abnormal or excessive bone loss, or with abnormal or reduced bone resorption, or with abnormal calcium metabolism.

Combinations of conjugate compounds according to the invention, or for use according to the invention, and other therapies useful in the prevention or treatment of conditions or disorders associated with abnormal or excessive bone loss, or with abnormal or reduced bone resorption, or with abnormal calcium metabolism may be administered separately or in conjunction. The administration of one agent or conjugate compound may be prior to, concurrent to, or subsequent to the administration of other agent(s) or conjugate compounds.

In alternative embodiments, while the conjugate compounds according to the invention may themselves be considered "prodrugs," the conjugate compounds may be supplied as further prodrug or protected forms, which release the compound after administration to a subject. For example, the compound may carry a protective group which is split off by hydrolysis in body fluids, e.g., in the bloodstream, thus releasing the active compound or is oxidized or reduced in body fluids to release the compound. Accordingly, a "prodrug" is meant to indicate a compound that may be converted under physiological conditions (e.g., enzymatically) or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a subject.

The term "prodrug" is also meant to include any covalently bonded carriers which release the active compound of the invention in vivo when such prodrug is administered to a subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and acetamide, formamide, and benzamide derivatives of amine functional groups in the compounds of the invention and the like.

A discussion of prodrugs may be found in "Smith and Williams' Introduction to the Principles of Drug Design," H. J. Smith, Wright, Second Edition, London (1988); Bundgard, H., *Design of Prodrugs* (1985), pp. 7-9, 21-24 (Elsevier, Amsterdam); The Practice of Medicinal Chemistry, Camille G. Wermuth et al., Ch 31, (Academic Press, 1996); A Textbook of Drug Design and Development, P. Krogsgaard-Larson and H. Bundgaard, eds. Ch 5, pgs 113 191 (Harwood Academic Publishers, 1991); Higuchi, T., et al., "Pro-drugs as Novel Delivery Systems," A.C.S. Symposium Series, Vol. 14; or in Bioreversible Carriers in Drug Design, ed. Edward B. Roche, American Pharmaceutical Association and Pergamon Press, 1987, all of which are incorporated in full by reference herein.

Suitable prodrug forms of the compounds of the invention include embodiments in which one of the hydroxyl groups is substituted with C(O)OR, where R is optionally substituted alkyl, alkenyl, alkynyl, aryl, or heteroaryl. In these cases the ester groups may be hydrolyzed in vivo (e.g. in bodily fluids), releasing the active compounds.

Conjugate compounds according to the invention, or for use according to the invention, can be provided alone or in combination with other compounds in the presence of a liposome, an adjuvant, or any pharmaceutically acceptable carrier, diluent or excipient, in a form suitable for administration to a subject such as a mammal, for example, humans, cattle, sheep, etc. If desired, treatment with a compound according to the invention may be combined with more traditional and existing therapies for the therapeutic indications described herein. Compounds according to the invention may be provided chronically or intermittently. "Chronic" administration refers to administration of the compound(s) in a continuous mode as opposed to an acute mode, so as to maintain the initial therapeutic effect (activity) for an extended period of time. "Intermittent" administration is treatment that is not consecutively done without interruption, but rather is cyclic in nature. The terms "administration," "administrable," or "administering" as used herein should be understood to mean providing a compound of the invention to the subject in need of treatment.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that has been approved, for example, by the United States Food and Drug Administration or other governmental agency as being acceptable for use in humans or domestic animals.

The compounds of the present invention may be administered in the form of pharmaceutically acceptable salts. In such cases, pharmaceutical compositions in accordance with this invention may comprise a salt of such a compound, preferably a physiologically acceptable salt, which are known in the art. In some embodiments, the term "pharmaceutically acceptable salt" as used herein means an active ingredient comprising conjugate compounds of Formula I or II used in the form of a salt thereof, particularly where the salt form confers on the active ingredient improved pharmacokinetic properties as compared to the free form of the active ingredient or other previously disclosed salt form.

A "pharmaceutically acceptable salt" includes both acid and base addition salts. A "pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

A "pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Thus, the term "pharmaceutically acceptable salt" encompasses all acceptable salts including but not limited to acetate, lactobionate, benzenesulfonate, laurate, benzoate, malate, bicarbonate, maleate, bisulfate, mandelate, bitartarate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of the compounds of the present invention can be used as a dosage for modifying solubility or hydrolysis characteristics, or can be used in sustained release or prodrug formulations. Also, pharmaceutically acceptable salts of the compounds of this invention may include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

Pharmaceutical formulations will typically include one or more carriers acceptable for the mode of administration of the preparation, be it by injection, inhalation, topical administration, lavage, or other modes suitable for the selected treatment. Suitable carriers are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The table or capsule may be enteric coated, or in a formulation for sustained release. Many suitable formulations are known, including, polymeric or protein microparticles encapsulating a compound to be released, ointments, gels, hydrogels, or solutions which can be used topically or locally to administer a compound. A sustained release patch or implant may be employed to provide release over a prolonged period of time. Many techniques known to skilled practitioners are described in *Remington: the Science & Practice of Pharmacy* by Alfonso Gennaro, $20^{th}$ ed., Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The conjugate compounds or pharmaceutical compositions according to the present invention may be administered by oral or non-oral, e.g., intramuscular, intraperitoneal, intravenous, intracisternal injection or infusion, subcutaneous injection, transdermal or transmucosal routes. In some embodiments, conjugate compounds or pharmaceutical compositions in accordance with this invention or for use in this invention may be administered by means of a medical device or appliance such as an implant, graft, prosthesis, stent, etc. Implants may be devised which are intended to contain and release such compounds or compositions. An example would be an implant made of a polymeric material adapted to release the conjugate compound, or its individual components, over a period of time. The conjugate compounds may be administered alone or as a mixture with a pharmaceutically acceptable carrier e.g., as solid formulations such as tablets, capsules, granules, powders, etc.; liquid formulations such as syrups, injections, etc.; injections, drops, suppositories, pessaries. In some embodiments, conjugate compounds or pharmaceutical compositions in accordance with this invention or for use in this invention may be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

The conjugate compounds of the invention may be used to treat animals, including mice, rats, horses, cattle, sheep, dogs, cats, and monkeys. However, compounds of the invention can also be used in other organisms, such as avian species (e.g., chickens). The compounds of the invention may also be effective for use in humans. The term "subject" or alternatively referred to herein as "patient" is intended to be referred to an animal, preferably a mammal, most preferably a human, who has been the object of treatment, observation or experiment. However, the conjugate compounds, methods and pharmaceutical compositions of the present invention may be used in the treatment of animals. Accordingly, as used herein, a "subject" may be a human, non-human primate, rat, mouse, cow, horse, pig, sheep, goat, dog, cat, etc. The subject may be suspected of having or at risk for having a condition or disorder associated with abnormal or excessive bone loss, or with abnormal or reduced bone resorption, or with abnormal calcium metabolism.

An "effective amount" of a compound according to the invention includes a therapeutically effective amount or a prophylactically effective amount. A "therapeutically effective amount" refers to an amount effective, at dosages and for periods of time necessary, to achieve the desired therapeutic result, such as inhibition of bone resorption, stimulation of bone growth, or treatment of any condition described herein. A therapeutically effective amount of a compound may vary according to factors such as the disease state, age, sex, and weight of the individual, and the ability of the compound to elicit a desired response in the individual.

Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as inhibition of bone resorption, stimulation of bone growth, or prevention of any condition described herein. Typically, a prophylactic dose is used in subjects prior to or at an earlier stage of disease, so that a prophylactically effective amount may be less than a therapeutically effective amount. A suitable range for therapeutically or prophylactically effective amounts of a compound may be any value from 0.1 nM-0.1M, 0.1 nM-0.05M, 0.05 nM-15 µM or 0.01 nM-10 µM.

In alternative embodiments, in the treatment or prevention of conditions which require modulation of bone growth or resorption, or calcium metabolism, an appropriate dosage level will generally be about 0.01 to 1000 mg per kg subject body weight per day, and can be administered in single or multiple doses. In some embodiments, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. In general, compounds of the invention should be used without causing substantial toxicity, and as described herein, the compounds exhibit a suitable safety profile for therapeutic use. Toxicity of the compounds of the invention can be determined using standard techniques, for example, by testing in cell cultures or experimental animals and determining the therapeutic index, i.e., the ratio between the $LD_{50}$ (the dose lethal to 50% of the population) and the LD100 (the dose lethal to 100% of the population). In some circumstances however, such as in severe disease conditions, it may be necessary to administer substantial excesses of the compositions.

Various alternative embodiments and examples of the invention are described herein. These embodiments and examples are illustrative and should not be construed as limiting the scope of the invention.

The present invention will be further illustrated in the following example(s).

EXAMPLE

General $^1$H and $^{13}$C NMR spectra were recorded with a Bruker Avance II 600 MHz spectrometer using a TCI cryoprobe, an Avance III 500 MHz spectrometer using a TXI inverse probe, or an Avance III 400 MHz spectrometer using a BBOF+ATM probe. NMR data processing was performed with MestRecNova software (MestreLab Research, ver. 6.0.4-5850). The spectra were referenced to the corresponding solvent signals (H. E. Gottlieb, V. Kotlyar, A. Nudelman, "NMR Chemical Shifts of Common Laboratory Solvents as Trace Impurities" *J. Org. Chem.*, 62 (1997) 7512-7515). LC-MS were recorded with an ESI ion source on an Agilent 6200 Time-of-Flight spectrometer coupled with Agilent 1200 series front-end. Analytical thin-layer chromatography (TLC) was performed on aluminum plates pre-coated with silica gel 60F-254 as the adsorbent (EMD). The developed plates were air-dried, exposed to UV light and/or dipped in KMnO$_4$ solution (http://www[dot]chemistry[dot]mcmaster[dot]ca/adronov/resources/Stains_for_Developing_TLC-_Plates.pdf) and heated. Flash chromatography was performed on a BioTage Isolera instrument using HP-silica cartridges from BioTage or SiliCycle Inc. Derivatized silica was obtained from SiliCycle Inc. Tetrahydrofuran (THF) was distilled from Na and benzophenone under nitrogen. Dichloromethane (DCM) was distilled from CaH$_2$ under nitrogen. Pyridine, triethylamine (TEA), and diisopropylethylamine (DIPEA) were distilled from CaH$_2$ under nitrogen. Other reagents and solvents were obtained from commercial vendors and used as received.

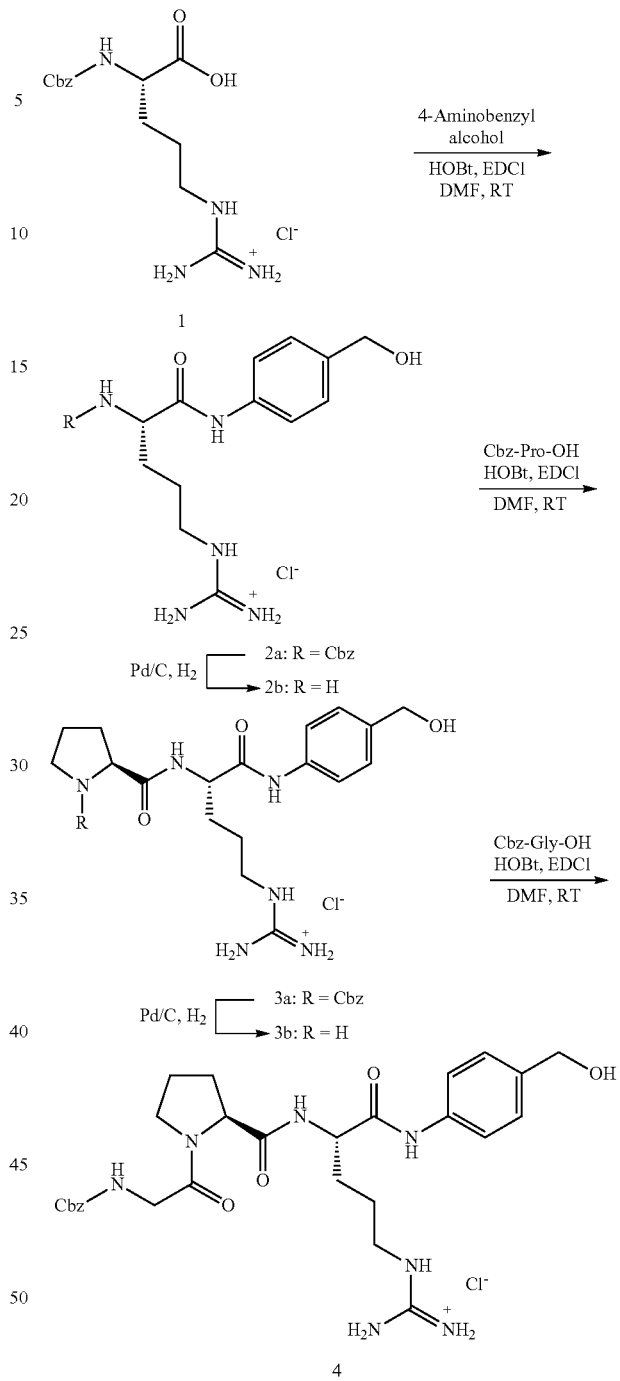

(S)-amino((4-(((benzyloxy)carbonyl)amino)-5-((4-(hydroxymethyl)phenyl)amino)-5-oxopentyl)amino)methaniminium (2a)

Cbz-Arg-OH (3.448 g, 10 mmol), HOBT (1.531 g, 10 mmol), 4-aminobenzylalcohol (1.232 g, 10 mmol) and EDCl (2.300 g, 10 mmol) was dissolved in 50 mL DMF. 4.0 hour later, the solvent DMF was removed by high vacuum. The residue was separated by column chromatography 120 g silica gel (gradient: methanol/dichloromethane 5% to 34%), then solvent was removed by rotavap and got 3.985 g light brown solid. $^1$H NMR (500 MHz, DMSO) δ 10.20 (s, 1H), 7.87 (t, J=5.4 Hz, 1H), 7.61 (dd, J=14.4, 8.1 Hz, 3H), 7.39-7.29 (m, 5H), 7.24 (d, J=8.4 Hz, 2H), 5.14 (t, J=5.7 Hz, 1H), 5.08-4.95 (m, 2H), 4.43 (d, J=5.6 Hz, 2H), 4.19 (dd, J=13.7, 8.3 Hz, 1H), 3.12 (dd, J=12.8, 6.5 Hz, 2H), 1.84-1.70 (m, 1H), 1.69-1.41 (m, 3H). $^{13}$C NMR (126 MHz, DMSO) δ 170.65, 156.92, 156.03, 137.54, 137.46, 136.96, 128.35, 127.80, 127.71, 126.85, 118.97, 65.46, 62.57, 54.92, 40.13, 28.94, 25.21. HRMS (ESI) calcd for $C_{21}H_{28}N_5O_4^+$ (MH$^+$) 414.2136. found 414.2149.

amino(((S)-4-((S)-1-((benzyloxy)carbonyl)pyrrolidine-2-carboxamido)-5-((4-(hydroxymethyl)phenyl)amino)-5-oxopentyl)amino)methaniminium (3a)

Compound 2a (0.827 g, 2 mmol) was dissolved in 20 mL methanol, palladium on carbon (10%) (0.083 g) was added to the solution. With uniform stirring atmospheric pressure hydrogen was passed through the solution. 2.0 hour later, TLC indicated completed consumption of start material. The reaction mixture was filtered by celite, after that methanol was removed by rotavap. The residue, Cbz-Pro-OH (0.500 g, 2 mmol), HOBT (0.306 g, 2 mmol) and EDCl (0.460 g, 2.4 mmol) was dissolved in 10 mL DMF. 4.0 hour later, the reaction solvent DMF was removed by high vacuum. The residue was separated by column chromatography 50 g silica gel (gradient: methanol/dichloromethane 5% to 34%), then solvent was removed by rotavap and got 0.970 g off-white solid. $^1$H NMR (600 MHz, DMSO) δ 10.15 (d, J=130.0 Hz, 1H), 8.86 (d, J=46.9 Hz, 1H), 8.55-8.35 (m, 2H), 7.71 (s, 3H), 7.55 (dd, J=19.9, 8.3 Hz, 2H), 7.44-7.16 (m, 7H), 5.04 (ddd, J=42.0, 41.2, 12.9 Hz, 2H), 4.43 (s, 2H), 4.40-4.24 (m, 2H), 3.09 (ddd, J=17.7, 12.3, 5.9 Hz, 1H), 3.00 (dt, J=12.5, 6.8 Hz, 1H), 2.23-2.07 (m, 1H), 1.91-1.32 (m, 7H). $^{13}$C NMR (151 MHz, DMSO) δ 172.21 (d, J=40.9 Hz), 170.40 (d, J=4.9 Hz), 167.13 (s), 157.36 (s), 154.04 (d, J=66.9 Hz), 137.66-137.35 (m), 136.93 (d, J=1.1 Hz), 128.32 (d, J=29.5 Hz), 127.67 (d, J=40.3 Hz), 127.23 (d, J=71.3 Hz), 126.92 (s), 118.96 (d, J=2.6 Hz), 65.90 (d, J=25.5 Hz), 62.60 (s), 59.46 (d, J=131.4 Hz), 52.84 (d, J=7.8 Hz), 46.88 (d, J=83.0 Hz), 40.06 (s), 30.63 (d, J=165.3 Hz), 28.92 (d, J=35.8 Hz), 24.95 (d, J=12.9 Hz), 23.50 (d, J=134.8 Hz). HRMS (ESI) calcd for $C_{26}H_{35}N_6O_5^+$ (MH$^+$) 511.2663. found 511.2674.

amino(((S)-4-((S)-1-(((benzyloxy)carbonyl)glycyl)pyrrolidine-2-carboxamido)-5-((4-(hydroxymethyl)phenyl)amino)-5-oxopentyl)amino)methaniminium chloride (4)

Compound 3a (0.300 g, 0.587 mmol) was dissolved in 10 mL methanol, palladium on carbon (10%) (0.030 g) was added to the solution. With uniform stirring atmospheric pressure hydrogen was passed through the solution. 2.0 hour later, TLC indicated completed consumption of start material. The reaction mixture was filtered by celite, after that methanol was removed by rotavap. The residue, Cbz-Gly-OH (0.133 g, 0.636 mmol), HOBT (0.091 g, 0.594 mmol) and EDCl (0.132 g, 0.689 mmol) was dissolved in 10 mL DMF. 4.0 hour later, the reaction solvent DMF was removed by high vacuum. The residue was separated by column chromatography 12 g silica gel (gradient: methanol/dichloromethane 5% to 34%), then solvent was removed by rotavap and got 0.333 g off-white solid. HRMS (ESI) calcd for $C_{28}H_{38}N_7O_6^+$ (MH$^+$) 568.2878. found 568.2888.

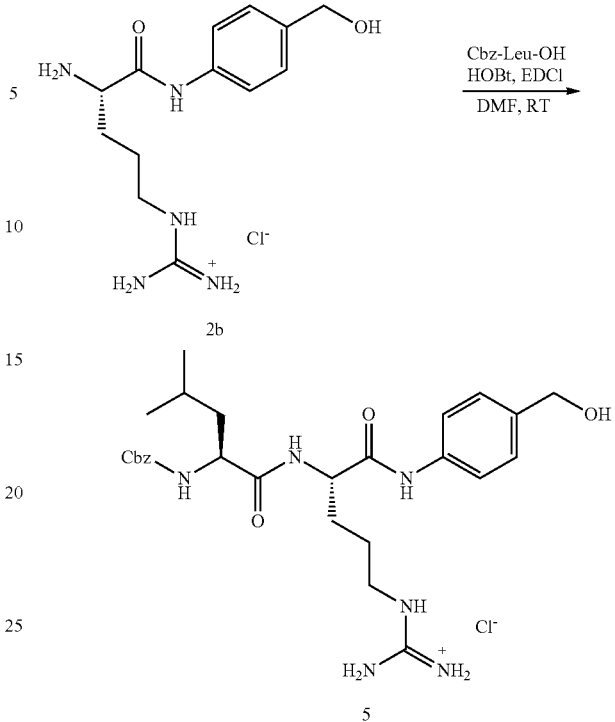

(5S,8S)-13-amino-8-((4-(hydroxymethyl)phenyl)carbamoyl)-5-isobutyl-3,6-dioxo-1-phenyl-2-oxa-4,7,12-triazatridecan-13-iminium chloride (5)

Compound 2a (0.625 g, 1.580 mmol) was dissolved in 20 mL methanol, palladium on carbon (10%) (0.063 g) was added to the solution. With uniform stirring atmospheric pressure hydrogen was passed through the solution. 2.0 hour later, TLC indicated completed consumption of start material. The reaction mixture was filtered by celite, after that methanol was removed by rotavap. The residue, Cbz-Leu-OH (0.421 g, 1.587 mmol), HOBT (0.303 g, 1.979 mmol) and EDCl (0.303 g, 1.581 mmol) was dissolved in 45 mL DMF. 12.0 hour later, the reaction solvent DMF was removed by high vacuum. The residue was separated by column chromatography 50 g silica gel (gradient: methanol/dichloromethane 5% to 34%), then solvent was removed by rotavap and got 0.760 g off-white solid. $^1$H NMR (500 MHz, DMSO) δ 10.19 (s, 1H), 8.15 (d, J=7.8 Hz, 1H), 7.91 (t, J=5.6 Hz, 1H), 7.58 (d, J=8.4 Hz, 2H), 7.49 (d, J=8.2 Hz, 1H), 7.44 (s, 1H), 7.33 (dt, J=19.6, 4.2 Hz, 7H), 7.26-7.21 (m, 3H), 5.06-4.93 (m, 2H), 4.53-4.31 (m, 3H), 4.09 (td, J=9.1, 5.6 Hz, 1H), 3.14 (dd, J=12.3, 6.1 Hz, 2H), 1.86-1.72 (m, 1H), 1.69-1.32 (m, 6H), 0.86 (t, J=7.2 Hz, 6H). $^{13}$C NMR (126 MHz, DMSO) δ 172.46, 170.17, 156.96, 155.96, 137.54, 137.46, 137.05, 128.33, 127.74, 127.58, 126.86, 118.95, 65.37, 62.56, 53.24, 52.76, 40.65, 40.08, 29.23, 25.07, 24.22, 23.10, 21.41. HRMS (ESI) calcd for $C_{27}H_{39}N_6O_5^+$ (MH$^+$) 527.2976. found 527.2994.

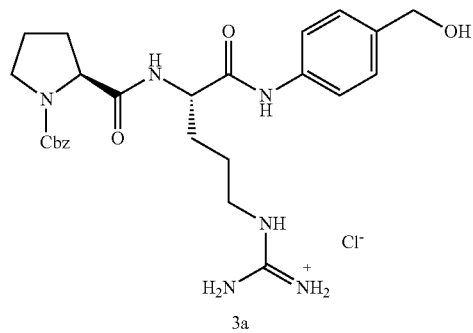

3a

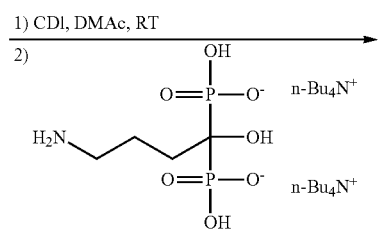

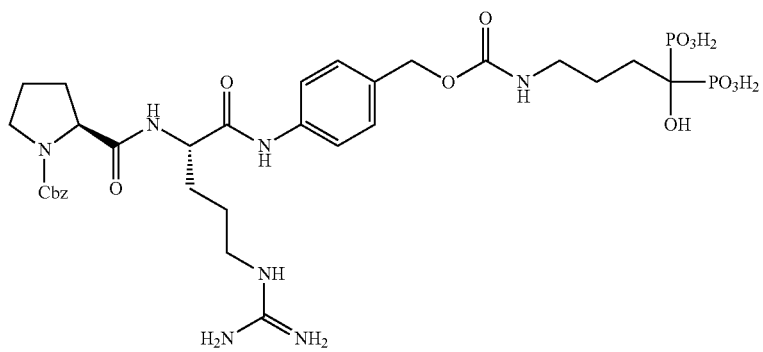

6

(4-((((4-(((S)-2-((S)-1-((benzyloxy)carbonyl)pyrrolidine-2-carboxamido)-5-guanidinopentanamido)benzyl)oxy)carbonyl)amino)-1-hydroxybutane-1,1-diyl)bis(phosphonic acid) (6)

Compound 5 (51 mg, 0.100 mmol), CDI (25 mg, 0.154 mmol) was dissolved in 0.5 mL DMF. The mixture was stirred at room temperature, 2.0 hour later HPLC indicated completed consumption of start material. After that alendronic acid stock solution (230 mg, 0.160 mmol) was added, the mixture was stirred at room temperature for 4.0 hours. The reaction mixture was treated with anion-exchange column (Strong Anion Ex Silicycle R66430B, Lot 53470). First, it was washed with ACN/H$_2$O=1/1 (5.0 column volume). Second, it was wash with water (2.0 column volume). Last, product was eluted by NaCl solution (5.0%). The NaCl then was removed by C18 column. After freeze drying, we got product as white power (40 mg). $^1$H NMR (500 MHz, DMSO) δ 7.61 (t, J=8.4 Hz, 2H), 7.45-7.20 (m, 7H), 5.09-4.95 (m, 2H), 4.90 (s, 1H), 4.40-4.22 (m, 2H), 3.48-3.29 (m, 2H), 3.03 (d, J=6.3 Hz, 1H), 2.91 (t, J=6.9 Hz, 2H), 2.14 (d, J=8.5 Hz, 1H), 1.74 (dd, J=33.2, 27.3 Hz, 8H), 1.60-1.33 (m, 3H). HRMS (ESI) calcd for C$_{31}$H$_{46}$N$_7$O$_{13}$P$_2^+$ (MH$^+$) 786.2623. found 786.2650.

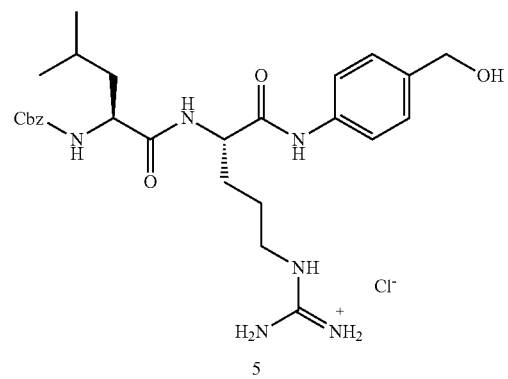

5

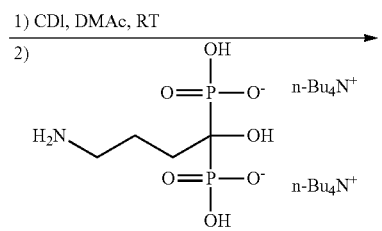

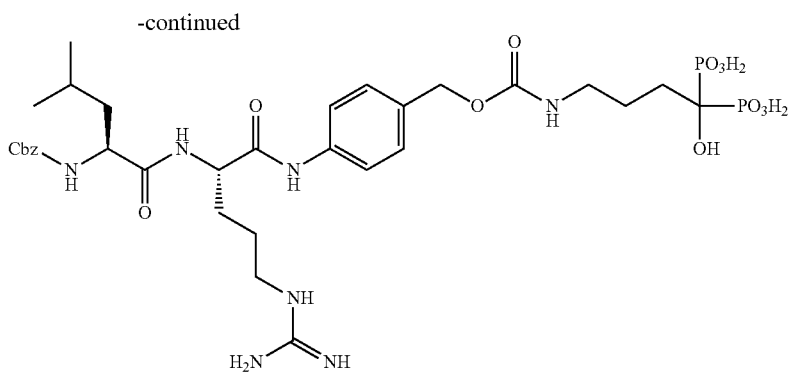

7

4-(((((4-((S)-2-((S)-2-(((benzyloxy)carbonyl)amino)-4-methylpentanamido)-5-guanidinopentanamido)benzyl)oxy)carbonyl)amino)-1-hydroxybutane-1,1-diyl)bis(phosphonic acid) (7)

Compound 5 (54 mg, 0.102 mmol), CDI (25 mg, 0.154 mmol) was dissolved in 0.5 mL DMF. The mixture was stirred at room temperature, 2.0 hour later HPLC indicated completed consumption of start material. After that alendronic acid stock solution (230 mg, 0.160 mmol) was added, the mixture was stirred at room temperature for 4.0 hours. The reaction mixture was treated with anion-exchange column (Strong Anion Ex Silicycle R66430B, Lot 53470). First, it was washed with ACN/H$_2$O=1/1 (5.0 column volume). Second, it was wash with water (2.0 column volume). Last, product was eluted by NaCl solution (5.0%). The NaCl was then removed by C18 column. After freeze drying, we got product as white power (40 mg). $^1$H NMR (500 MHz, DMSO) δ 7.60 (d, J=8.3 Hz, 2H), 7.28 (dd, J=34.4, 6.8 Hz, 7H), 5.03-4.95 (m, 2H), 4.90 (s, 2H), 4.40 (dd, J=8.9, 5.2 Hz, 1H), 4.05 (dd, J=9.5, 5.4 Hz, 1H), 3.11 (t, J=6.5 Hz, 2H), 2.91 (t, J=6.8 Hz, 2H), 1.87-1.71 (m, 3H), 1.71-1.50 (m, 5H), 1.49-1.35 (m, 3H), 0.89-0.74 (m, 6H). HRMS (ESI) calcd for $C_{32}H_{50}N_7O_{13}P_2^+$ (MH$^+$) 802.2936. found 802.2964.

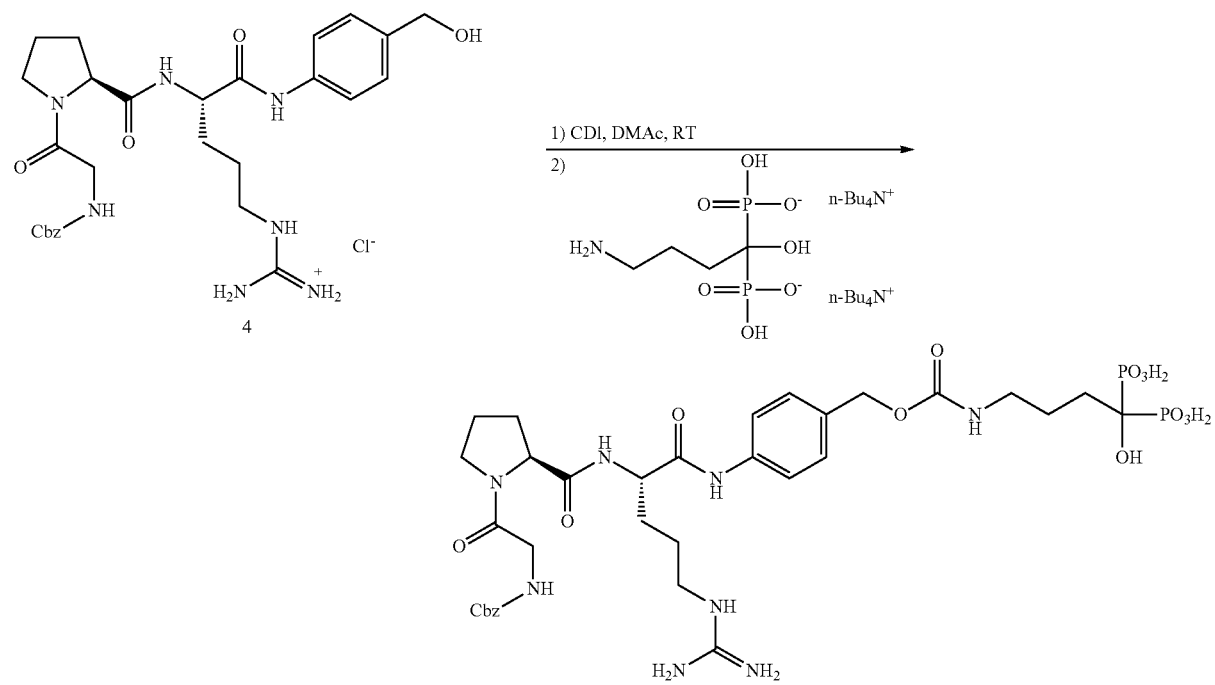

(4-(((((4-((S)-2-((S)-1-(((benzyloxy)carbonyl)glycyl)pyrrolidine-2-carboxamido)-5-guanidinopentanamido)benzyl)oxy)carbonyl)amino)-1-hydroxybutane-1,1-diyl)bis(phosphonic acid) (8)

Compound 4 (76 mg, 0.134 mmol), CDI (46 mg, 0.284 mmol) was dissolved in 0.8 mL DMF. The mixture was stirred at room temperature, 2.0 hour later HPLC indicated completed consumption of start material. After that alendronic acid stock solution (310 mg, 0.228 mmol) was added, the mixture was stirred at room temperature for 4.0 hours. The reaction mixture was treated with anion-exchange column (Strong Anion Ex Silicycle R66430B, Lot 53470). First, it was washed with ACN/H$_2$O=1/1 (5.0 column volume). Second, it was wash with water (2.0 column volume). Last, product was eluted by NaCl solution (5.0%). The NaCl was then removed by C18 column. After freeze drying, we got product as white power (60 mg). $^1$H NMR (500 MHz, DMSO) δ 7.67 (d, J=8.4 Hz, 2H), 7.43-7.17 (m, 7H), 4.97 (ddd, J=39.4, 19.7, 9.6 Hz, 4H), 4.33 (dd, J=8.8, 4.1 Hz, 2H), 3.86 (s, 2H), 3.66-3.33 (m, 2H), 3.12 (t, J=6.5 Hz, 2H), 2.92 (t, J=6.9 Hz, 2H), 2.06 (dt, J=16.3, 8.0 Hz, 1H), 1.98-1.41 (m, 11H). HRMS (ESI) calcd for $C_{33}H_{49}N_8O_{14}P_2^+$ (MH$^+$) 843.2838. found 843.2876.

Stability of 6, 7 and 8 in Rat Plasma and Serum

Figure 4A:
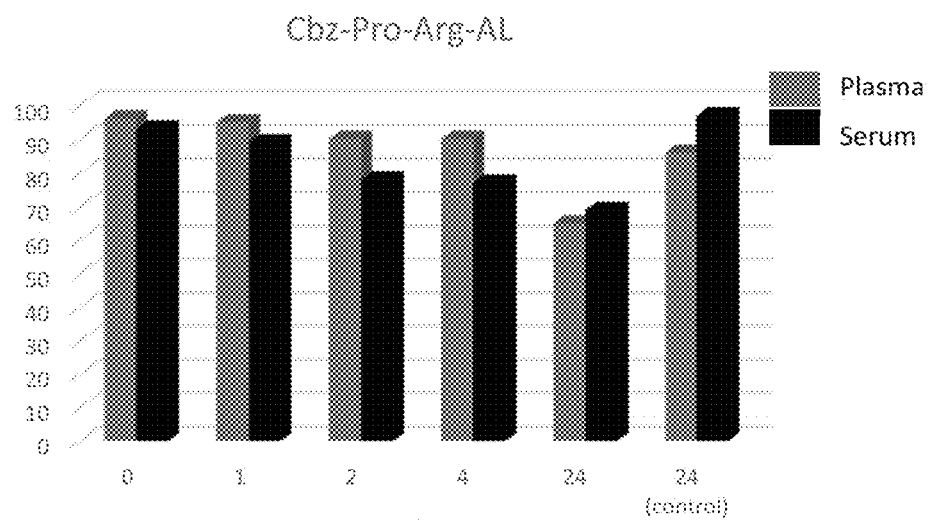
FIGS. 4A-C are bar graphs showing the stability of compounds 6 (Cbz-Pro-Arg-AL, FIG. 4A), 7 (Cbz-Leu-Arg-AL, FIG. 4B), and 8 (Cbz-Gly-Pro-Arg-AL, FIG. 4C), in rat plasma and serum at 37° C.
Figure 4B:
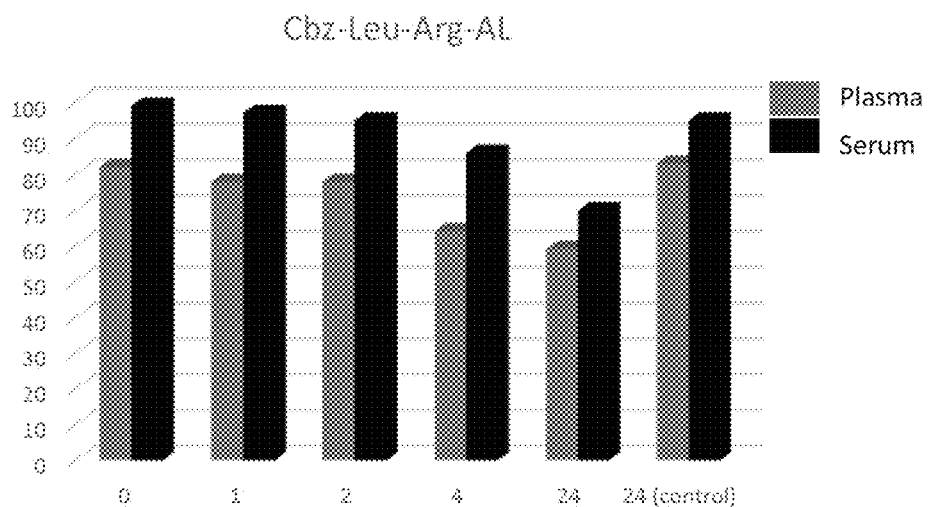
Figure 4C:
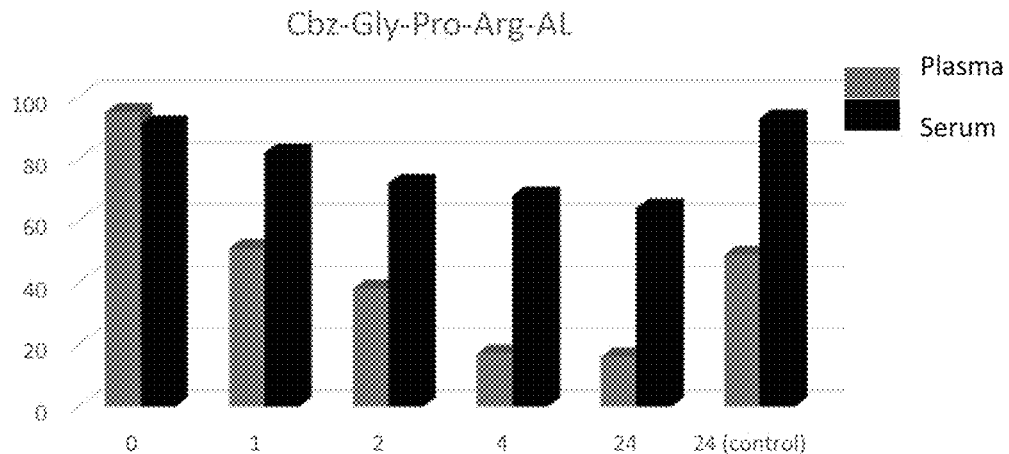

A stock solution of 6, 7 and 8 (10 mM in water) was used to prepare 100 uL solutions of 6, 7 and 8 (100 uM) in fresh and inactive rat plasma (inactived by 56 C for 2.0 hour), fresh and inactive rat serum (inactived by 56 C for 2.0 hour). The samples were incubated in a 37 C water bath for 24 h. Samples were analyzed at time points 0, 1, 2, 4, 24 hour. At each time point methanol (1.0 M HCl, 100 uL) was added, the resulting mixture was centrifuged and the supernatant solution was analyzed by HPLC (Phenomenex Monolith C18, 4.6×50 mm, on ACN-water-TFA gradient, signal=254 nm) to assess the remains concentration of 6, 7 and 8. Table 1 and FIGS. 4A-C show the stability of compounds 6, 7, and 8, respectively, in rat plasma and serum at 37° C.

TABLE 1

| Time (hour) | PR, 6 (%) | | LR, 7 (%) | | GPR, 8 (%) | |
|---|---|---|---|---|---|---|
| | Plasma | Serum | Plasma | Serum | Plasma | Serum |
| 0 | 96 | 93 | 82 | 99 | 95 | 91 |
| 1 | 95 | 89 | 78 | 97 | 51 | 82 |
| 2 | 90 | 78 | 78 | 95 | 38 | 72 |
| 4 | 90 | 77 | 64 | 86 | 17 | 68 |
| 24 | 65 | 69 | 59 | 70 | 16 | 64 |
| 24 (control) | 86 | 97 | 83 | 95 | 49 | 93 |

General Procedure for Cathepsin K Assays.

Procathepsin K human was obtained from Sigma-Aldrich (recombinant, expressed in *E. coli*, ≥95% (SDS-PAGE)). Cathepsin K rat (recombinant, expressed in *E. coli*) was obtained from Merck as a gift. A stock solution of 6, 7 and 8 (1.0 mM in water) was used to prepare 100 uL solutions of 6, 7 and 8 (100 uM). Enzyme activity was assayed using the Cathepsin K standard substrate Z-Leu-Arg-AMC. Assay buffer: 50 mM MES, pH 5.5, 2 mM EDTA, 4 mM DTT, 0.15% Chondroitin sulfate. Final concentration in 100 ul: human or rat Cathepsin K 0.2 uM, standard substrate Z-Leu-Arg-AMC 100 uM, conjugates 6, 7 and 8 100 uM. Procathepsin K human was activated in 50 mM Sodium Acetate, pH 4.1, 200 mM NaCl at room temperature for 40 min. Reaction were analyzed at time points 1, 2, 20 hour at 37 C, 20 uL injections were analyzed by HPLC 4.6×150 mm C18 column on MeOH-water-NH$_3$.H$_2$O gradient, signal=240 nm. The appearances of released self-immolative linker 4-aminobenyl alcohol were recorded. Conjugates hydrolysis rates were calculated according to the appearance of 4-aminobenyl alcohol and its DTT trapped compound. Table 2 shows the stability of compounds 6, 7, and 8 in the presence of human Cathepsin K and rat Cathepsin K at 37° C.

TABLE 2

| | PR, 6 (%) | | LR, 7 (%) | | GPR, 8 (%) | |
|---|---|---|---|---|---|---|
| Time (hour) | Hum CatK | Rat CatK | Hum CatK | Rat CatK | Hum CatK | Rat CatK |
| 1 | 90 | 5 | 66 | 73 | 91 | 11 |
| 2 | 98 | 10 | 75 | 80 | 100 | 20 |
| 20 | | 52 | 79 (3 hour) | 95 | | 80 |

Standard substrate Z-Leu-Arg-AMC: in Rat CatK 71% 6 min, in Hum CatK 63% 6 min.

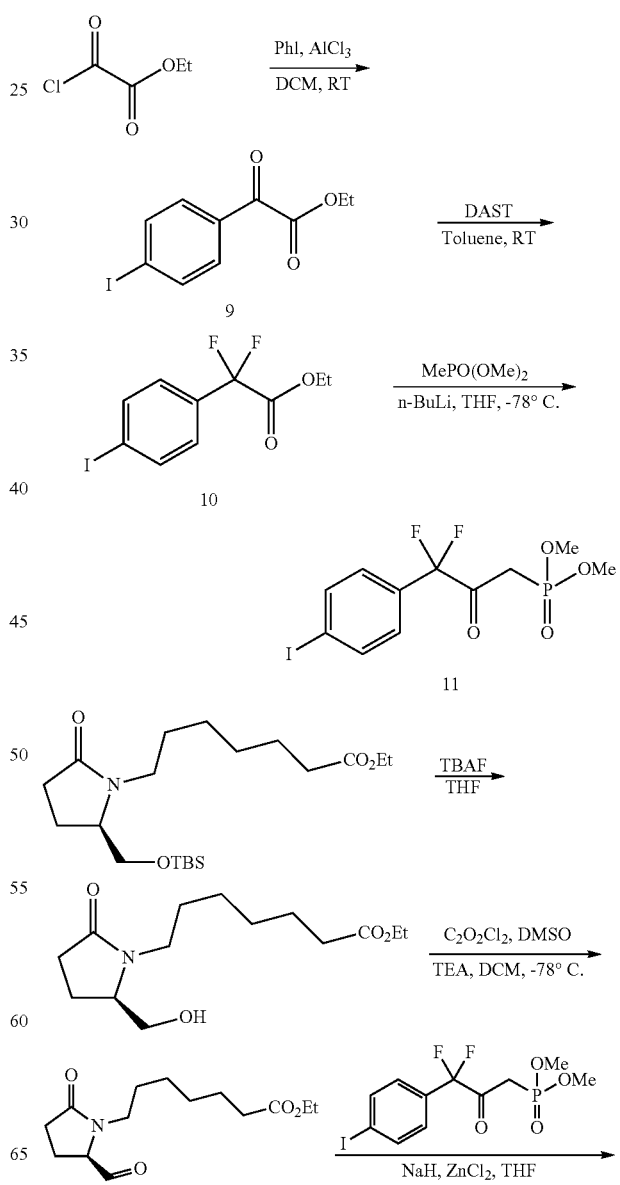

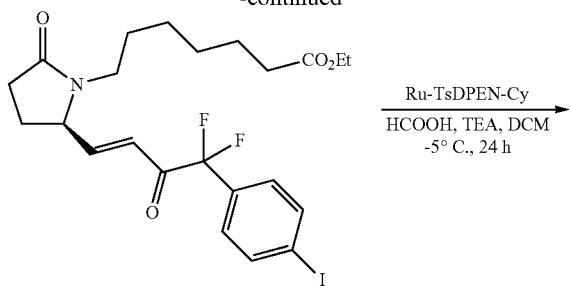

Ethyl 2-(4-iodophenyl)-2-oxoacetate (9)

Ethyloxalyl chloride (8.187 g, 60 mmol) was added dropwise at RT to a solution of iodobenzene (11.000 g, 54 mmol) and aluminium chloride (8.000 g, 60 mmol) in dichloromethane (100 ml) within 15 minutes. The mixture was left to stir at 23° C. for 3 hours. The reaction mixture was then poured onto ice-cold 3N hydrochloric acid. The mixture was then stirred for a further 10 minutes and then extracted with dichloromethane. The organic phase was washed with 1 N hydrochloric acid and saturated aqueous sodium chloride solution, dried over sodium sulphate and concentrated under reduced pressure. The crude product was chromatographed on silica gel. 5.6 g of product were obtained. $^1$H NMR (500 MHz, CDCl$_3$) δ 7.89 (d, J=8.5 Hz, 1H), 7.73 (d, J=8.5 Hz, 1H), 4.44 (q, J=7.0 Hz, 1H), 1.42 (t, J=7.2 Hz, 2H).

Ethyl 2,2-difluoro-2-(4-iodophenyl)acetate (10)

Compound 9 (5.600 g, 18.4 mmol) in toluene (10 mL) was treated with DAST (3.262 g, 20.2 mmol) (drop-wise over 15 min). The reaction mixture stirred at RT overnight. Ice-water-NH$_3$.H$_2$O (5 mL) was added by drop-wise to quench the reaction. Then the solution was extract by MTBE (20 mL*2). At last, the MTBE solution was dried by MgSO$_4$ and rotavapped. The crude product was chromatographed on silica gel. 3.1 g of product were obtained. $^1$H NMR (500 MHz, CDCl$_3$) δ 7.81 (d, J=8.6 Hz, 2H), 7.34 (d, J=8.6 Hz, 2H), 4.30 (q, J=7.1 Hz, 2H), 1.30 (t, J=7.1 Hz, 3H). $^{19}$F NMR (471 MHz, CDCl$_3$) δ -104.37 (s).

Dimethyl (3,3-difluoro-3-(4-iodophenyl)-2-oxopropyl)phosphonate (11)

Dimethyl methylphosphonate (1.300 g, 10.5 mmol) in THF (40 mL) was cooled to -78 C. Then the solution was treated with n-BuLi (1.6M in hexane) (6.6 mL, 10.5 mmol), stirred at -78 C for half hour. Compound 10 (3.10 g, 9.5 mmol) in THF (20 mL) was added by drop-wise. The reaction mixture stirred at -78 C for four hours. After that quenched the reaction mixture with CH$_3$COOH (0.630 g, 10.5 mmol) at -78 C. Let it worm to RT. 60 mL NH$_4$Cl (aq.) and 30 mL water was added. Extracted with Ethyl acetate (30 mL*3). The organic phase was dry by MgSO$_4$, filtered and concentrated. The crude product was purified by chromatographed on silica gel. (Gradient: ethyl acetate/hexane 50% to 100%), got product as light yellow solid (2.755 g). $^1$H NMR (400 MHz, CDCl$_3$) δ 7.82 (d, J=8.6 Hz, 1H), 7.28 (d, J=8.5 Hz, 1H), 3.75 (d, J=11.3 Hz, 3H), 3.36 (d, J=22.0 Hz, 1H).

Ethyl (R,E)-7-(2-(4,4-difluoro-4-(4-iodophenyl)-3-oxobut-1-en-1-yl)-5-oxopyrrolidin-1-yl)heptanoate (12)

Compound 11 (2.738 g, 6.77 mmol) in THF (60 mL) was treated with NaH (0.284 g, 7.1 mmol). Half hour later, the reaction was cooled to 0 C, then treated with ethyl (R)-7-(2-formyl-5-oxopyrrolidin-1-yl)heptanoate (1.825 g, 6.77 mmol) in THF (30 mL), followed by ZnCl$_2$ (1.9 M in 2-methyltetrahydrofuran), then the mixture was heated to 50 C. Six hour later, quenched the reaction with sat. NH$_4$Cl. Extracted with Ethyl acetate (50 mL*3). The organic phase was dry by MgSO$_4$, filtered and concentrated. The crude product was purified by chromatographed on silica gel. (Gradient: ethyl acetate/hexane 50% to 100%), got product as light yellow oil (2.70 g). $^1$H NMR (500 MHz, CDCl$_3$) δ 7.82 (d, J=8.4 Hz, 2H), 7.27 (d, J=8.4 Hz, 2H), 6.96 (dd, J=15.6, 7.7 Hz, 1H), 6.57 (d, J=15.6 Hz, 1H), 4.24 (td, J=7.9, 4.6 Hz, 1H), 4.12 (q, J=7.1 Hz, 3H), 3.56 (ddd, J=13.9, 8.9, 7.0 Hz, 1H), 2.76 (ddd, J=13.9, 8.7, 5.3 Hz, 1H), 2.45-2.33 (m, 2H), 2.31-2.24 (m, 3H), 1.84-1.76 (m, 1H), 1.63-1.56 (m, 2H), 1.50-1.35 (m, 2H), 1.31-1.23 (m, 7H).

Ethyl 7-((R)-2-((R,E)-4,4-difluoro-3-hydroxy-4-(4-iodophenyl)but-1-en-1-yl)-5-oxopyrrolidin-1-yl)heptanoate (13)

Compound 12 (2.70 g, 4.93 mmol), Et$_3$N (0.787 mL, 4.93 mmol) and HCOOH (0.223 mL, 5.92 mmol) was dissolved in dichloromethane (20 mL). Then the mixture was cooled to -5 C, followed by Ru-TsDPEN-Cy (0.094 g, 0.148 mmol). The reaction stirred at -5 C overnight. At last, quenched the reaction with sat. NaHCO$_3$. Extracted with Ethyl acetate (50 mL*3). The organic phase was dry by MgSO$_4$, filtered and concentrated. The crude product was purified by chromatographed on silica gel. (Gradient: ethyl acetate/hexane 50% to 100%), got product as light yellow oil (2.0 g) $^1$H NMR (500 MHz, CDCl$_3$) δ 7.77 (d, J=8.4 Hz, 2H), 7.21 (d, J=8.4 Hz, 2H), 5.71-5.63 (m, 2H), 4.54 (td, J=9.7, 3.0 Hz, 1H), 4.11 (q, J=7.1 Hz, 2H), 4.06-4.00 (m, 1H), 3.41 (ddd, J=13.8, 8.8, 6.8 Hz, 1H), 2.75 (ddd, J=13.9, 8.7, 5.4 Hz, 1H), 2.38-2.25 (m, 4H), 2.22-2.13 (m, 1H), 1.70-1.56 (m, 3H), 1.47-1.22 (m, 9H). HRMS (ESI) calcd for C$_{23}$H$_{31}$F$_2$INO$_4^+$ (MH$^+$) 550.1260. found 550.1267.

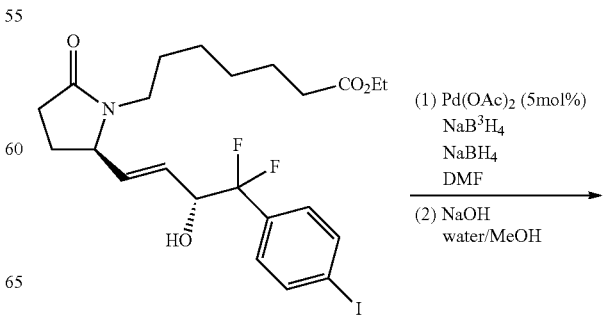

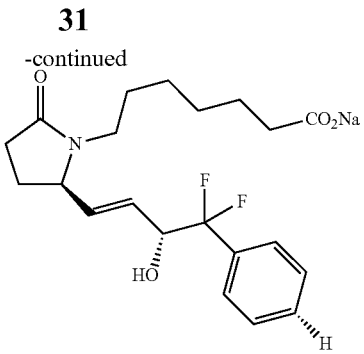

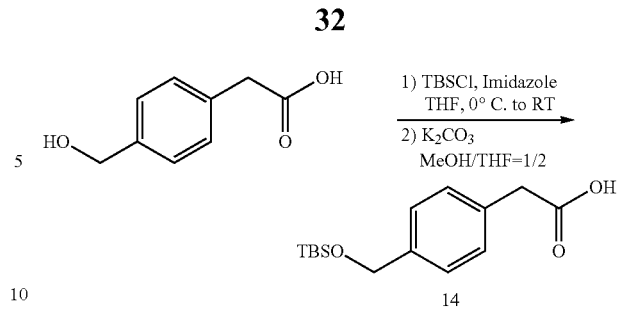

Sodium 7-((R)-2-((R, E)-4, 4-difluoro-3-hydroxy-4-(phenyl-4-t) but-1-en-1-yl)-5-oxopyrrolidin-1-yl) heptanoate Compound 13 (3.6 mg, 6.56 umol) in 100 uL DMF was treated with Pd(OAc)$_2$ (0.33 umol in 66 uL DMF), stirred 15 min. Then treated with NaB$^3$H$_4$(SA: 15.6 Ci/mmol) (12.13 mCi in 100 uL DMF), stirred 1.0 hour. Then treated with NaBH$_4$ (6.56 umol in 131 uL DMF), stirred 1.0 hour. 3 mL water was added to the reaction mixture to quench the reaction. The mixture was directly loaded on the C18 column. After wash with water (6 column volume), MeOH was used to wash the product out. The product in MeOH was treated with NaOH (1.0 M, 2.0 mL), stirred 30 min. Then remove MeOH by ratavap. The hydrolysis product in water was directly loaded on the C18 column. After wash with water (6 column volume), MeOH was used to wash the hydrolysis product out and counted 3.8 mCi. Radiochemical yield 31%.

2-(4-(((tert-butyldimethylsilyl)oxy)methyl)phenyl) acetic acid (14)

4-(Hydroxymethyl)phenylacetic acid (3.330 g, 20 mmol), imidazole (3.400 g, 50 mmol) was dissolved in THF (50 mL). Then it was put to ice-water bath. TBSCl (6.340 g, 42 mmol) was dissolved in THF (10 mL) and it was added drop-wise. The ice-water bath was removed when the dropping finished. 2.0 hours later, TLC indicated completed consumption of start material. Then 200 mL hexanes was added to the reaction mixture. After that the mixture was filtered and rotovapped. The residue was dissolved in MeOH (20 mL) and THF (40 mL). K$_2$CO$_3$ was added as solid. 2.0 hours later, the mixture was filtered and rotavapped. The residue was dissolved in 150 mL water, the pH was adjust to 2.0 used HCl. Then the solution was extract by MTBE (50 mL*2). At last, the MTBE solution was dried by MgSO$_4$ and rotavapped, got 5.52 g colourless oil as the product. $^1$H NMR (500 MHz, CDCl$_3$) δ 7.29 (d, J=8.1 Hz, 2H), 7.24 (d, J=8.1 Hz, 2H), 4.72 (s, 2H), 3.64 (s, 2H), 0.94 (s, 9H), 0.09 (s, 6H).

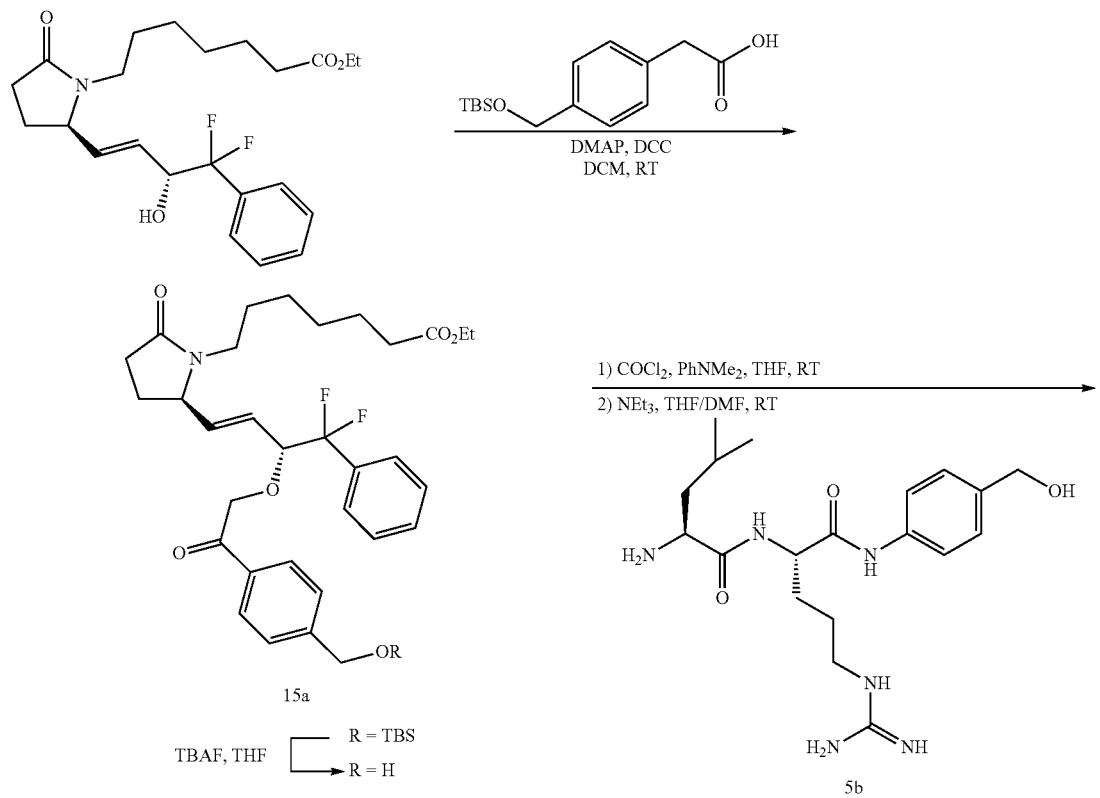

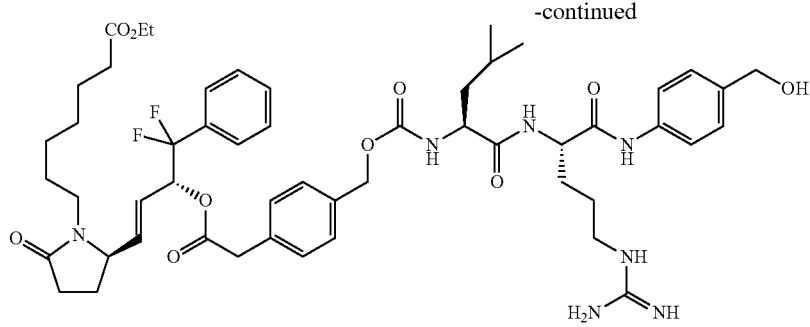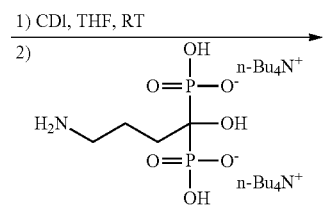

16a

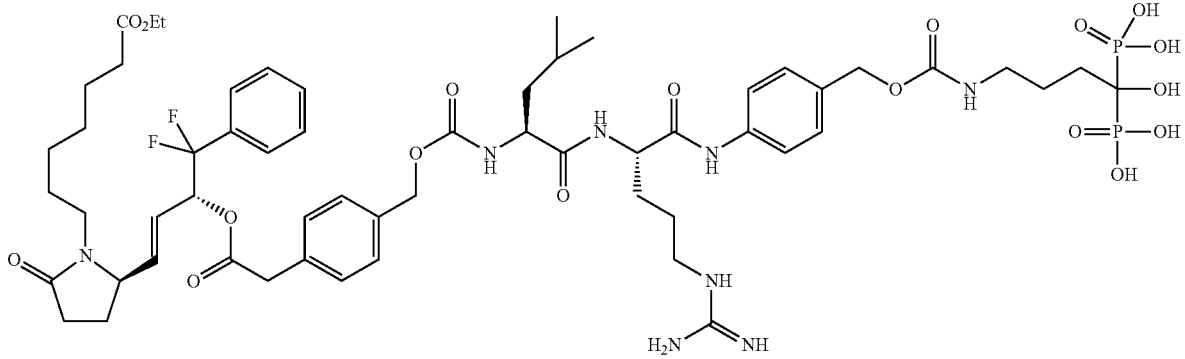

17a

Ethyl 7-((R)-2-((R,E)-3-(2-(4-(((tert-butyldimethyl-silyl)oxy)methyl)phenyl)-2-oxoethoxy)-4,4-difluoro-4-phenylbut-1-en-1-yl)-5-oxopyrrolidin-1-yl)heptanoate (15a)

Compound 14 (0.652 g, 2.325 mmol), EP4 agonist (0.847 g, 2.0 mmol), DMAP (0.024 g, 0.2 mmol) was dissolved in DCM. Then, the reaction mixture was treated with DCC (0.648 g, 3.141 mmol). 4.0 hour later, HPLC indicated completed consumption of start material. The reaction mixture was then filtered, the filtrate was rotavapped. After that the residue was separated by column chromatography of silica gel (1.0%-8.0%, MeOH/DCM). $^1$H NMR (500 MHz, DMSO) δ 7.46 (m, 5H), 7.22 (d, J=8.0 Hz, 2H), 7.11 (d, J=8.0 Hz, 2H), 5.80 (td, J=10.6, 6.6 Hz, 1H), 5.61 (ddd, J=23.8, 15.4, 7.5 Hz, 2H), 4.68 (s, 2H), 4.12-3.95 (m, 3H), 3.69 (q, J=15.4 Hz, 2H), 3.18 (dt, J=13.8, 7.7 Hz, 1H), 2.45 (ddd, J=13.4, 8.3, 5.3 Hz, 1H), 2.24 (t, J=7.4 Hz, 2H), 2.19-2.00 (m, 3H), 1.52-1.41 (m, 3H), 1.35-1.05 (m, 9H), 0.90 (s, 9H), 0.08 (s, 6H). HRMS (ESI) calcd for $C_{38}H_{54}F_2NO_6Si^+$ (MH$^+$) 686.3683. found 686.3700.

Ethyl 7-((R)-2-((R,E)-3-(2-(4-(((5S,8S)-13-amino-8-((4-(hydroxymethyl)phenyl)carbamoyl)-13-imino-5-isobutyl-3,6-dioxo-2-oxa-4,7,12-triazatridecyl)phenyl)acetoxy)-4,4-difluoro-4-phenylbut-1-en-1-yl)-5-oxopyrrolidin-1-yl)heptanoate (16a)

Compound 15 (0.320 g, 0.47 mmol) in THF (1.56 mL) was treated with TBAF (1.0 M in THF) 520 uL. 30 min. later, TLC indicated completed consumption of start material. Then 40 mL Saturated NH$_4$Cl was used to quench the reaction. Then the solution was extract by MTBE (30 mL*3). At last, the MTBE solution was dried by MgSO$_4$ and rotavapped, got 0.270 g colourless oil. This colourless oil (0.270 g, 0.48 mmol) and PhNMe$_2$ (0.133 mL, 1.05 mmol) in THF (2.4 mL) was treated with COCl$_2$ (0.38 mL, 0.53 mmol) (1.4 M in toluene), stirred 30 min. Compound 5b (0.188 g, 0.48 mmol) and Et$_3$N (0.295 mL, 2.12 mmol) was dissolved in DMF (2.4 mL). At last, the DMF solution was pour to the THF reaction mixture. After stirring three hour, the solvents was removed by high vacuum and the residue was was separated by column chromatography of silica gel (4%-30%, MeOH/DCM). $^1$H NMR (500 MHz, DMSO) δ 10.07 (s, 1H), 8.13 (d, J=7.5 Hz, 1H), 7.63 (s, 1H), 7.59-7.39 (m, 8H), 7.25 (t, J=8.2 Hz, 4H), 7.13 (d, J=7.6 Hz, 2H), 5.91-5.74 (m, 1H), 5.62 (ddd, J=23.6, 15.3, 7.6 Hz, 2H), 5.12 (s, 1H), 4.98 (dt, J=45.4, 22.8 Hz, 2H), 4.43 (s, 3H), 4.20-3.93 (m, 4H), 3.70 (q, J=15.3 Hz, 2H), 3.22-3.09 (m, 3H), 2.45 (d, J=8.2 Hz, 1H), 2.25 (t, J=7.2 Hz, 2H), 2.20-2.01 (m, 3H), 1.76 (m, 1H), 1.63 (d, J=6.1 Hz, 2H), 1.47 (dd, J=14.0, 7.1 Hz, 7H), 1.28 (s, 1H), 1.26-1.19 (m, 3H), 1.16 (t, J=7.1 Hz, 3H), 1.10 (d, J=7.0 Hz, 2H), 0.86 (t, J=7.0 Hz, 6H). HRMS (ESI) calcd for $C_{52}H_{70}F_2N_7O_{10}^+$ (MH$^+$) 990.5147. found 990.5154.

(4-(((((4-((S)-2-((S)-2-(((((4-(2-(((R,E)-4-((R)-1-(7-ethoxy-7-oxoheptyl)-5-oxopyrrolidin-2-yl)-1,1-difluoro-1-phenylbut-3-en-2-yl)oxy)-2-oxoethyl)benzyl)oxy)carbonyl)amino)-4-methylpentanamido)-5-guanidinopentanamido)benzyl)oxy)carbonyl)amino)-1-hydroxybutane-1,1-diyl)bis(phosphonic acid) (17a)

CDI (2.2 mg, 0.013 mmol) was dissolved in 50 uL THF, then compound 16a (10 mg, 0.011 mmol) was added to the CDI solution. The mixture was stirred at room temperature, 1.0 hour later HPLC indicated completed consumption of start material. After that alendronic acid stock solution (40 uL, 0.026 mmol) was added, the mixture was stirred at room temperature for 1.0 hours. The reaction mixture was quenched by CH$_3$COOH (3.0 uL, 0.052 mmol). Then it was diluted by 300 uL acetonitrile and water mixture (ACN/H$_2$O=1/1) before loading on anion-exchange column (Strong Anion Ex Silicycle R66430B, Lot 53470). First, it was washed with ACN/H$_2$O=1/1 (5.0 column volume). Then, product was eluted by KH$_2$PO$_4$—K$_2$HPO$_4$ solution (0.08M pH=8.0, ACN/H$_2$O=2/3). The salts was then removed by C18 column. After freeze drying, we got product as white power (6 mg). $^1$H NMR (600 MHz, DMSO) δ 7.55 (d, J=8.3 Hz, 2H), 7.49 (t, J=7.2 Hz, 1H), 7.42 (t, J=7.6 Hz, 2H), 7.37 (d, J=7.4 Hz, 2H), 7.27 (d, J=8.5 Hz, 2H), 7.22 (d, J=8.0 Hz, 2H), 7.09 (d, J=8.0 Hz, 2H), 5.75 (m, 1H), 5.69-5.50 (m, 2H), 5.11-4.86 (m, 4H), 4.42-4.36 (m, 1H), 4.03 (m, 4H), 3.65 (q, J=15.3 Hz, 2H), 3.18-3.08 (m, 3H), 2.93 (t, J=6.8 Hz, 2H), 2.46-2.41 (m, 1H), 2.22 (t, J=7.4 Hz, 2H), 2.18-2.11 (m, 2H), 2.06 (dd, J=12.6, 7.7 Hz, 1H), 1.86-1.78 (m, 2H), 1.75 (s, 1H), 1.71-1.58 (m, 4H), 1.57-1.40 (m, 7H), 1.25 (s, 1H), 1.18 (dd, J=14.7, 7.4 Hz, 3H), 1.13 (t, J=7.1 Hz, 3H), 1.07 (dd, J=15.2, 7.2 Hz, 2H), 0.83 (m, 6H). HRMS (ESI) calcd for C$_{57}$H$_{81}$F$_2$N$_8$O$_{18}$P$_2^+$ (MH$^+$) 1265.5107. found 1265.5088.

The general scheme for preparation of conjugate compound 17a is as follows.

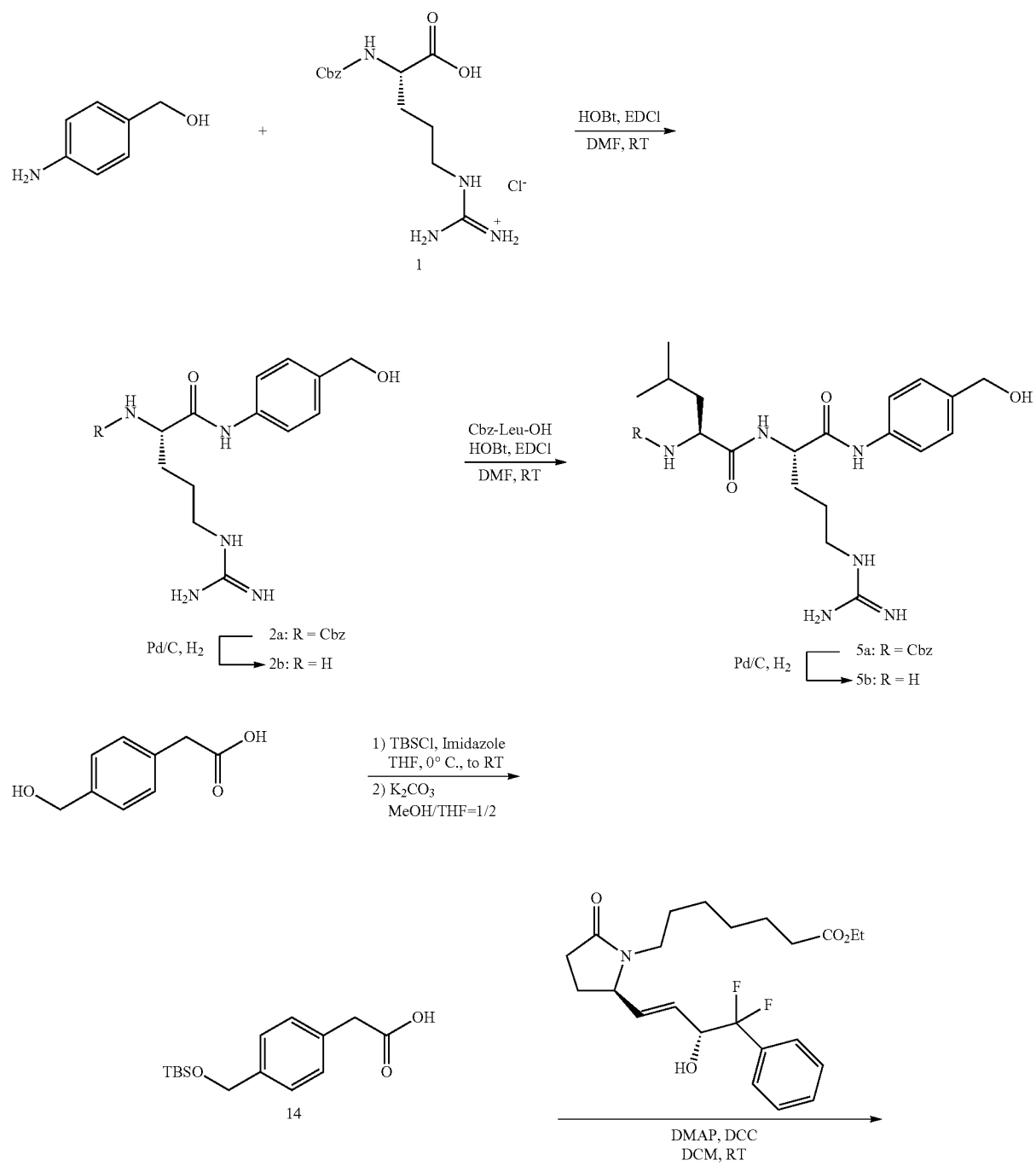

-continued
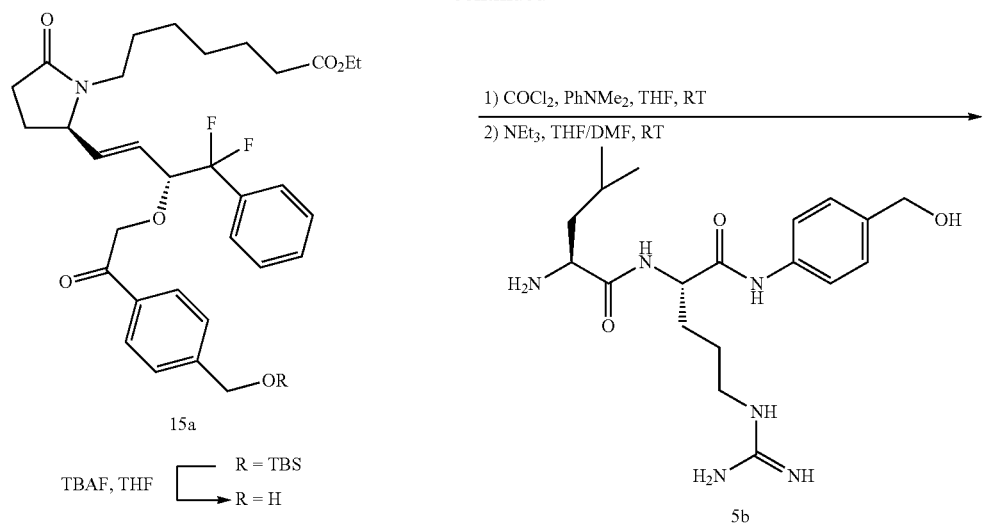
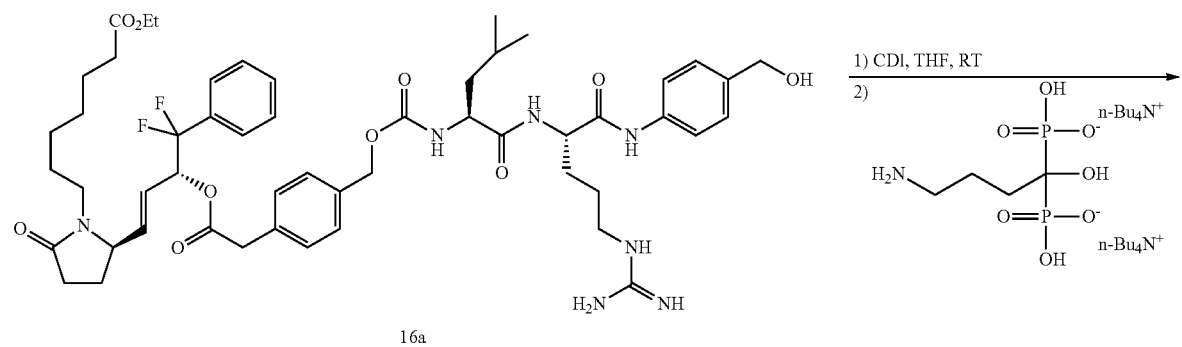
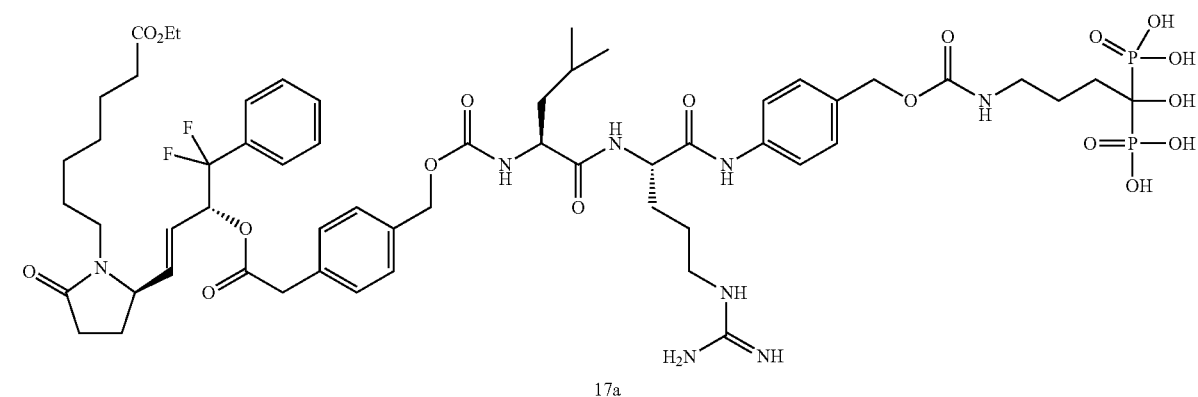
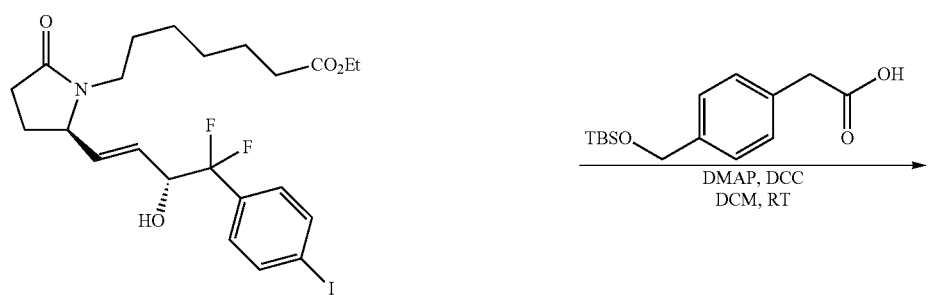

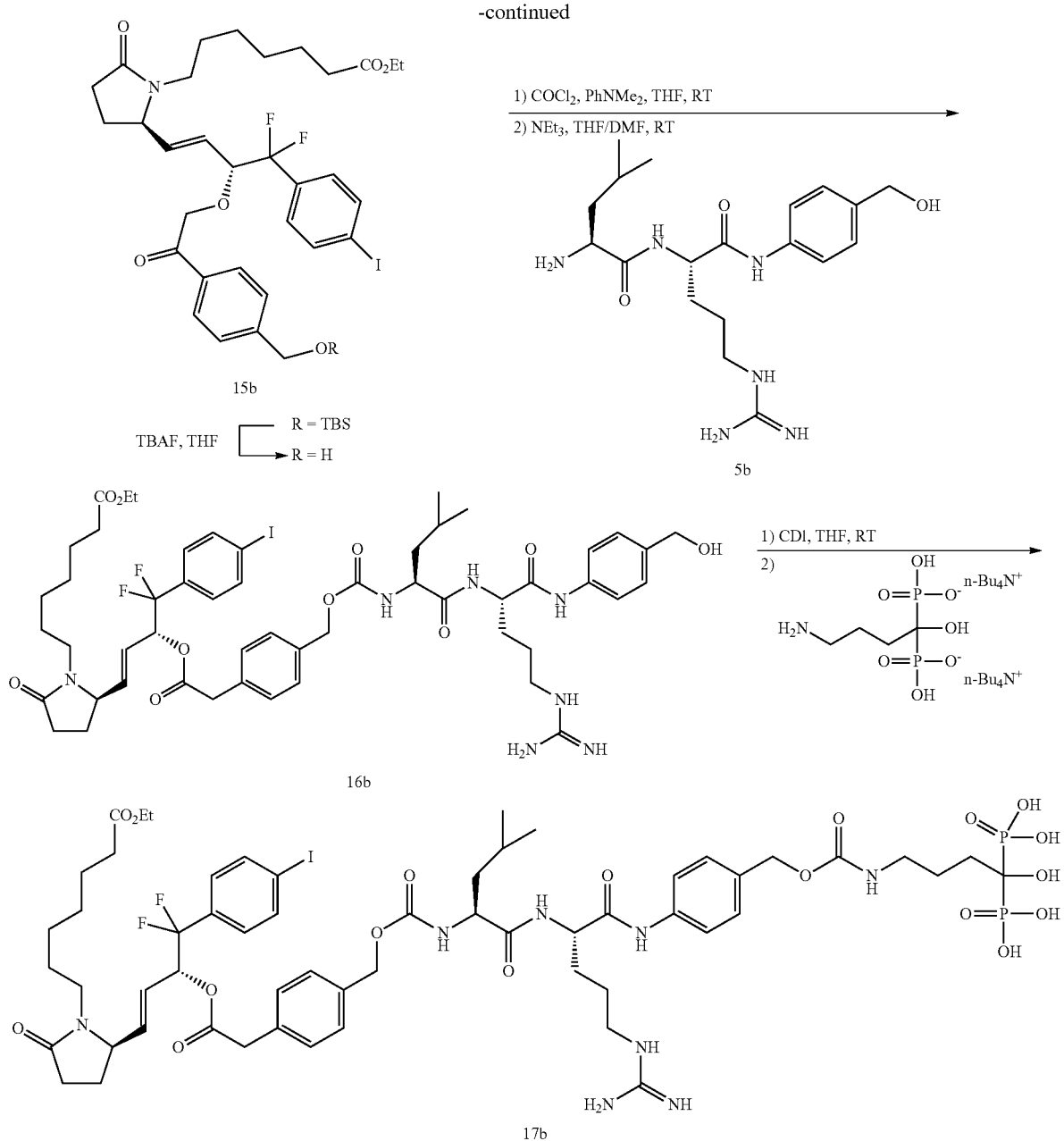

ethyl 7-((R)-2-((R,E)-3-(2-(4-(((tert-butyldimethylsilyl)oxy)methyl)phenyl)-2-oxoethoxy)-4,4-difluoro-4-(4-iodophenyl)but-1-en-1-yl)-5-oxopyrrolidin-1-yl)heptanoate (15b)

Compound 14 (0.652 g, 0.437 mmol), compound 13 (0.200 g, 0.364 mmol), DMAP (0.004 g, 0.036 mmol) was dissolved in DCM. Then, the reaction mixture was treated with DCC (0.113 g, 0.546 mmol). 4.0 hour later, HPLC indicated completed consumption of start material. The reaction mixture was then filtered, the filtrate was rotavapped. After that the residue was separated by column chromatography of silica gel (1.0%-8.0%, MeOH/DCM). $^1$H NMR (500 MHz, DMSO) δ 7.80 (d, J=8.1 Hz, 2H), 7.23 (d, J=7.8 Hz, 2H), 7.17 (d, J=8.2 Hz, 2H), 7.10 (d, J=7.9 Hz, 2H), 5.79 (dd, J=17.1, 10.8 Hz, 1H), 5.63 (ddd, J=23.7, 15.3, 7.3 Hz, 2H), 4.69 (s, 2H), 4.09-3.99 (m, 3H), 3.73-3.64 (m, 2H), 3.22-3.15 (m, 1H), 2.47-2.43 (m, 1H), 2.24 (t, J=7.3 Hz, 2H), 2.21-2.03 (m, 3H), 1.48 (dd, J=14.6, 7.3 Hz, 3H), 1.32-1.07 (m, 9H), 0.90 (s, 9H), 0.08 (s, 6H). HRMS (ESI) calcd for $C_{38}H_{53}F_2INO_6Si^+$ (MH$^+$) 812.2649. found.

ethyl 7-((R)-2-((R,E)-3-(2-(4-((5S,8S)-13-amino-8-((4-(hydroxymethyl)phenyl)carbamoyl)-13-imino-5-isobutyl-3,6-dioxo-2-oxa-4,7,12-triazatridecyl)phenyl)acetoxy)-4,4-difluoro-4-(4-iodophenyl)but-1-en-1-yl)-5-oxopyrrolidin-1-yl)heptanoate (16b)

Compound 15b (0.180 g, 0.222 mmol) in THF (0.50 mL) was treated with TBAF (1.0 M in THF) 240 uL. 30 min. later, TLC indicated completed consumption of start material. Then 40 mL Saturated NH$_4$Cl was used to quench the reaction. Then the solution was extract by MTBE (30 mL*3). At last, the MTBE solution was dried by MgSO$_4$ and rotavapped, got 0.155 g colourless oil. This colourless oil (0.155 g, 0.222 mmol) and PhNMe$_2$ (0.062 mL, 0.488 mmol) in THF (2.0 mL) was treated with COCl$_2$ (0.174 mL, 0.244 mmol) (1.4 M in toluene), stirred 30 min. Compound 5b (0.087 g, 0.48 mmol) and Et$_3$N (0.140 mL, 0.976 mmol) was dissolved in DMF (2.0 mL). At last, the DMF solution was pour to the THF reaction mixture. After stirring three hour, the solvents was removed by high vacuum and the residue was was separated by column chromatography of silica gel (4%-30%, MeOH/DCM). $^1$H NMR (500 MHz, DMSO) δ 10.07 (s, 1H), 8.14 (t, J=10.8 Hz, 1H), 7.82 (d, J=8.2 Hz, 2H), 7.63 (dd, J=11.2, 5.8 Hz, 1H), 7.56 (d, J=8.4 Hz, 2H), 7.46 (d, J=8.0 Hz, 1H), 7.30-7.19 (m, 6H), 7.13 (d, J=7.9 Hz, 2H), 5.80 (td, J=10.8, 6.6 Hz, 1H), 5.64 (ddd, J=23.8, 15.3, 7.5 Hz, 2H), 5.11 (t, J=5.6 Hz, 1H), 5.01 (dd, J=38.9, 12.7 Hz, 2H), 4.44 (t, J=8.0 Hz, 3H), 4.15-3.99 (m, 4H), 3.69 (q, J=15.6 Hz, 2H), 3.26-3.03 (m, 3H), 2.47-2.39 (m, 1H), 2.24 (q, J=7.4 Hz, 2H), 2.21-2.03 (m, 3H), 1.76 (m, 1H), 1.63 (dd, J=12.1, 6.2 Hz, 2H), 1.58-1.35 (m, 7H), 1.29 (dd, J=13.7, 5.8 Hz, 1H), 1.25-1.18 (m, 3H), 1.16 (t, J=7.1 Hz, 3H), 1.10 (dd, J=14.9, 7.7 Hz, 2H), 0.94-0.77 (m, 6H). HRMS (ESI) calcd for C$_{52}$H$_{69}$F$_2$IN$_7$O$_{10}$$^+$ (MH$^+$) 1116.4113. found 1116.4093.

(4-((((4-((S)-2-((S)-2-((((4-(2-(((R,E)-4-((R)-1-(7-ethoxy-7-oxoheptyl)-5-oxopyrrolidin-2-yl)-1,1-difluoro-1-(4-iodophenyl)but-3-en-2-yl)oxy)-2-oxoethyl)benzyl)oxy)carbonyl)amino)-4-methylpentanamido)-5-guanidinopentanamido)benzyl)oxy)carbonyl)amino)-1-hydroxybutane-1,1-diyl)bis(phosphonic acid) (17b)

CDI (2.0 mg, 0.012 mmol) was dissolved in 50 uL THF, then compound 16b (11 mg, 0.010 mmol) was added to the CDI solution. The mixture was stirred at room temperature, 1.0 hour later HPLC indicated completed consumption of start material. After that alendronic acid stock solution (40 uL, 0.024 mmol) was added, the mixture was stirred at room temperature for 1.0 hours. The reaction mixture was quenched by CH3COOH (3.0 uL, 0.052 mmol). Then it was diluted by 300 uL acetonitrile and water mixture (ACN/H$_2$O=1/1) before loading on anion-exchange column (Strong Anion Ex Silicycle R66430B, Lot 53470). First, it was washed with ACN/H$_2$O=1/1 (5.0 column volume). Then, product was eluted by KH$_2$PO$_4$—K$_2$HPO$_4$ solution (0.08M pH=8.0, ACN/H$_2$O=2/3). The salts was then removed by C18 column. After freeze drying, we got product as white power (6 mg). $^1$H NMR (600 MHz, DMSO) δ 9.02 (s, 1H), 7.79 (d, J=8.2 Hz, 2H), 7.63 (d, J=1.2 Hz, 1H), 7.57 (d, J=8.4 Hz, 2H), 7.27 (d, J=8.5 Hz, 2H), 7.24 (d, J=7.9 Hz, 2H), 7.19 (d, J=8.3 Hz, 2H), 7.09 (d, J=7.8 Hz, 2H), 5.75 (m, 1H), 5.69-5.50 (m, 2H), 5.11-4.86 (m, 4H), 4.42-4.36 (m, 1H), 4.03 (m, 4H), 3.65 (q, J=15.3 Hz, 2H), 3.18-3.08 (m, 3H), 2.93 (t, J=6.8 Hz, 2H), 2.46-2.41 (m, 1H), 2.22 (t, J=7.4 Hz, 2H), 2.18-2.11 (m, 2H), 2.06 (dd, J=12.6, 7.7 Hz, 1H), 1.86-1.78 (m, 2H), 1.75 (s, 1H), 1.71-1.58 (m, 4H), 1.57-1.40 (m, 7H), 1.25 (s, 1H), 1.18 (dd, J=14.7, 7.4 Hz, 3H), 1.13 (t, J=7.1 Hz, 3H), 1.07 (dd, J=15.2, 7.2 Hz, 2H), 0.83 (m, 6H). HRMS (ESI) calcd for C$_{57}$H$_{80}$F$_2$IN$_8$O$_{18}$P$_2$$^+$ (MH$^+$) 1391.4073. found 1391.4058.

Preparation of [$^3$H]-17a

Compound 17b (4.0 mg, 2.876 umol) in 100 uL DMF was treated with Pd(OAc)$_2$ (0.15 umol in 30 uL DMF), stirred 15 min. Then treated with NaB$^3$H$_4$ (NaBT$_4$)(SA: 10.9 Ci/mmol) (5.29 mCi, 1.53 umol in 50 uL DMF), stirred 1.0 hour. Then treated with NaBH$_4$ (2.0 umol in 20 uL DMF), stirred 1.0 hour. The reaction mixture was directly loaded on the C18 column. After wash with water (6 column volume), product was eluted by acetonitrile and water mixture (ACN/H$_2$O=1/1), and counted 0.56 mCi. Radiochemical yield 10.6%.

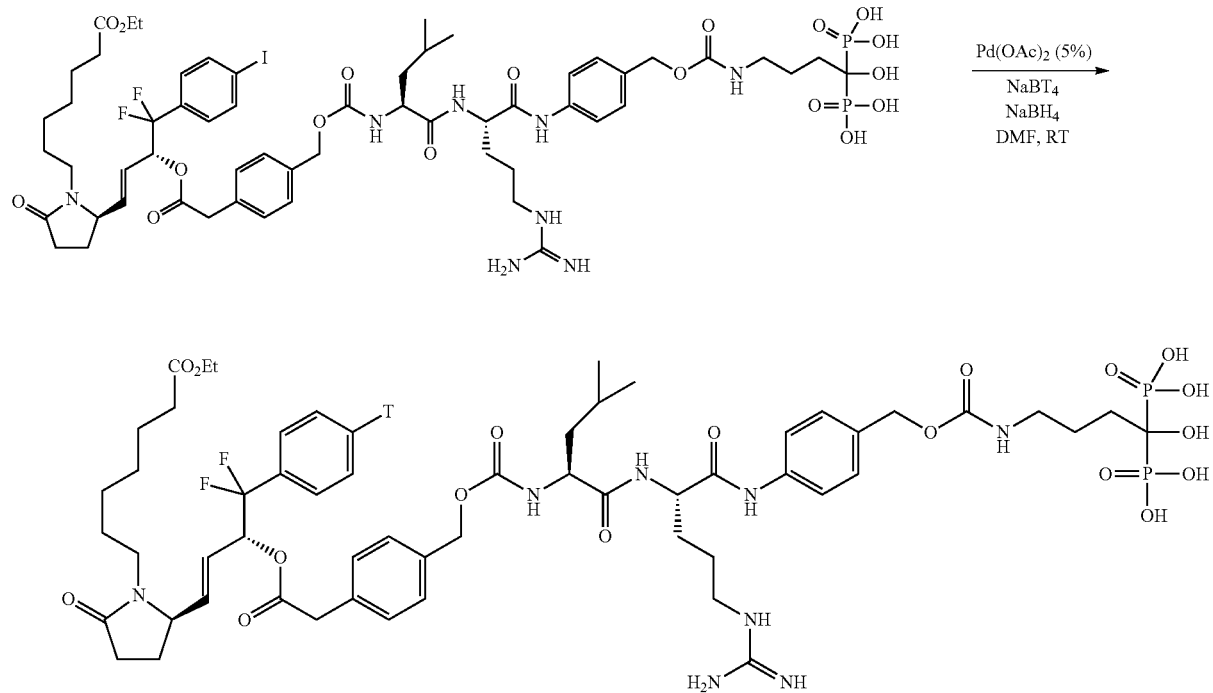

Preparation of [$^{14}$C]-17a

Figure 5:
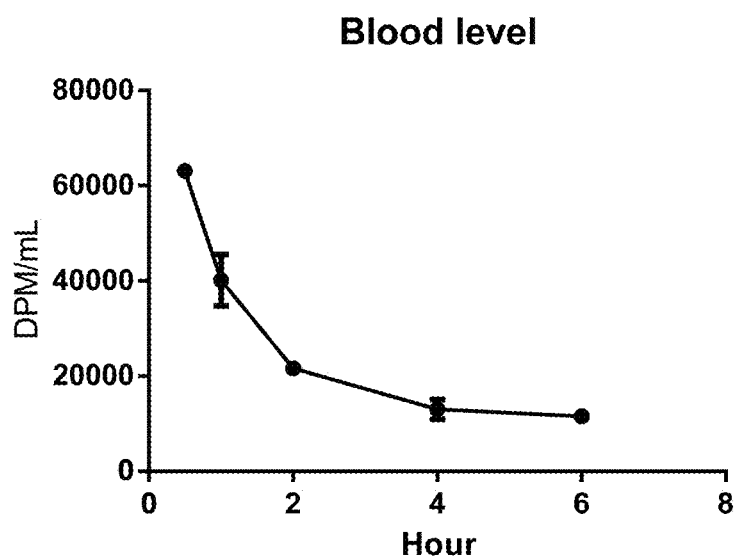
FIG. 5 is a line graph showing the level of tritiated compound 17a in blood.

CDI [carbonyl-$^{14}$C] (SA: 56 mCi/mmol) (8.9 umol, 0.5 mCi, 1.45 mg) was dissolved in 50 uL THF, then compound 16a (11 mg, 10 umol) was added to the CDI solution. The mixture was stirred at room temperature for 1.0 hour. After that alendronic acid stock solution (40 uL, 0.024 mmol) was added, the mixture was stirred at room temperature for 1.0 hours. The reaction mixture was quenched by CH$_3$COOH (3.0 uL, 0.052 mmol). Then it was diluted by 300 uL acetonitrile and water mixture (ACN/H$_2$O=1/1) before loading on anion-exchange column (Strong Anion Ex Silicycle R66430B, Lot 53470). First, it was washed with ACN/H$_2$O=1/1 (5.0 column volume). Then, product was eluted by KH$_2$PO$_4$—K$_2$HPO$_4$ solution (0.08M pH=8.0, ACN/H$_2$O=2/3). The salts was then removed by C18 column. The product as dissolved in 4.0 mL water i-PrOH mixture (ratio 1/1), and counted 0.26 mCi. Radiochemical yield 52%.

separated. 100 μL of the supernatant was analyzed in a Harvey OX-300 biological oxidizer using the four-minute program. The collected scintillation mixture was counted on a Beckman Coulter LS-6500 scintillation counter. The counting time was two minute. The results are shown in FIG. 5.

Rat Organ Distribution, Uptake and Release of Conjugate 17a in Rat Bone

After 6 h, 1, 7, 14, 28 days three animals were weighed, sacrificed by CO$_2$ and blood, fat, muscle, brain, heart, kidney, spleen, liver and bone were dissected and cleaned free of any loose tissue. The amount of radioactivity was determined by incineration in a R. J. Harvey OX300 Biological Oxidizer. The percent of the compound retained in the skeleton and the other organs at each time point was calculated by measuring activity per gram (μCi/g) in the collected samples and extrapolating to total activity retained in the skeleton and the other organs, the weight of skeleton was calculated by 8% of the body weight, the weight of the

Figure 6:
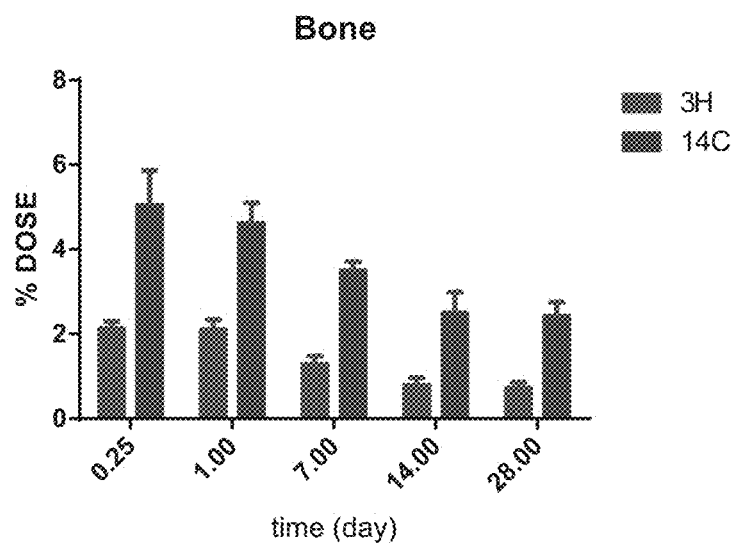
FIG. 6 is a bar graph showing the level of tritiated compound 17a in bone.
Figure 7A:
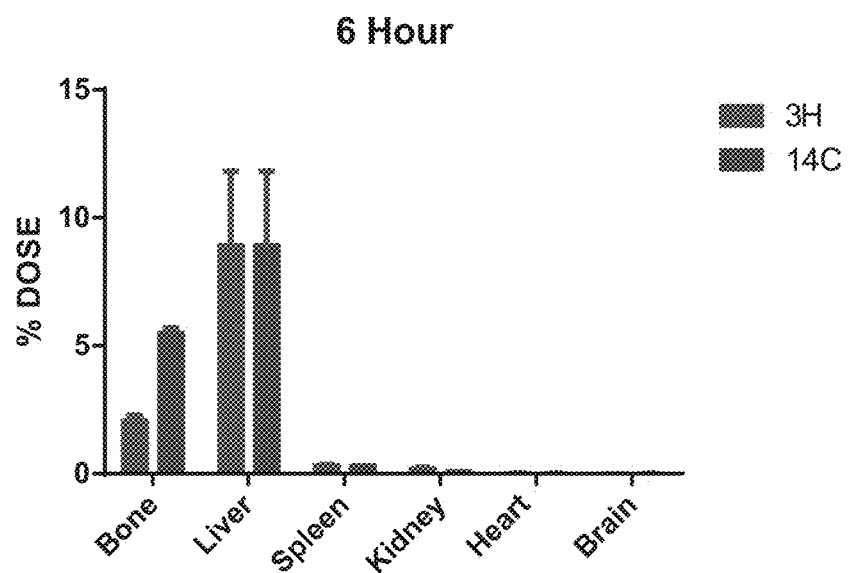
FIGS. 7A-E—are bar graphs showing the level of tritiated compound 17a in various organs at different time points (6 hours, FIG. 7A; 1 day, FIG. 7B; 7 days, FIG. 7C; 14 days, FIG. 7D; 28 days, FIG. 7E).
Figure 7B:
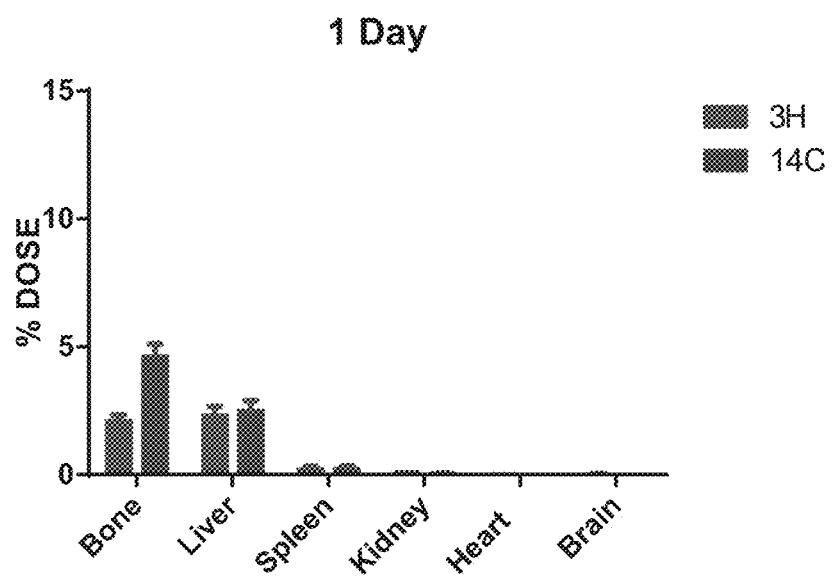
Figure 7C:
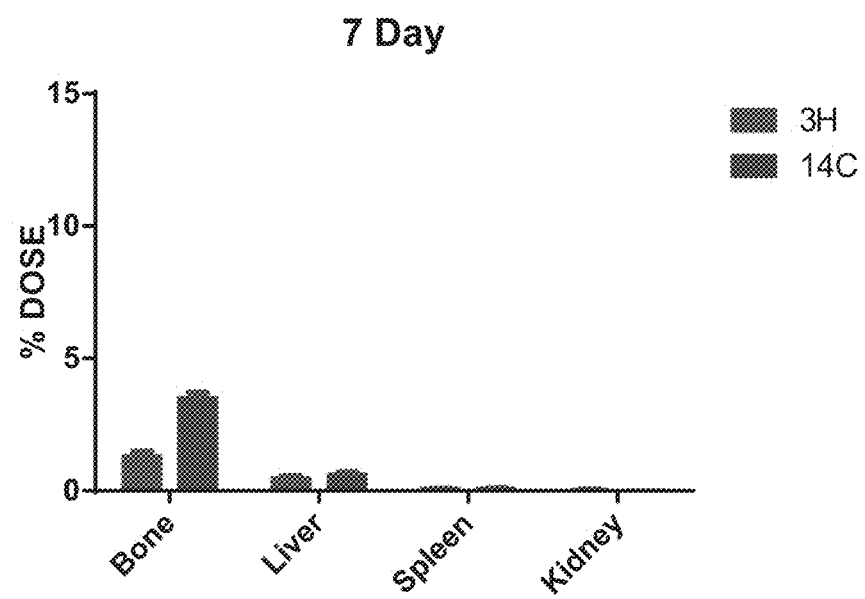
Figure 7D:
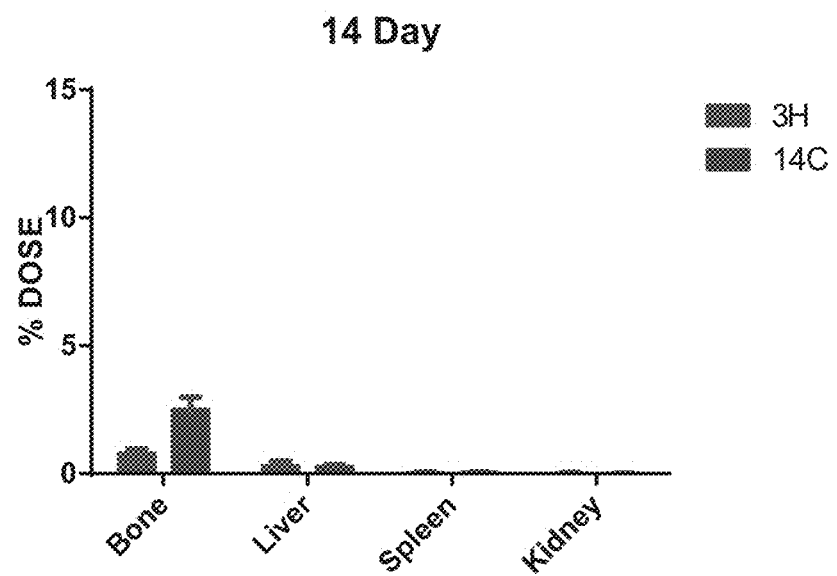
Figure 7E:
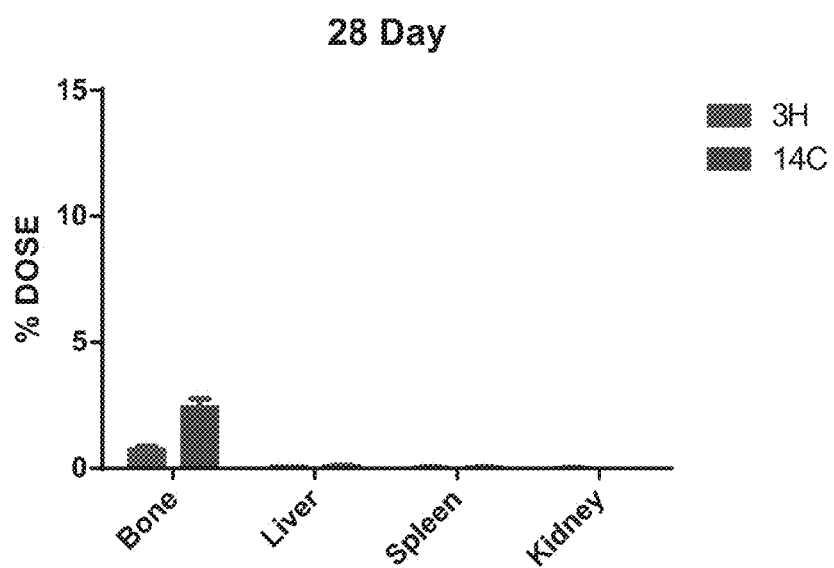

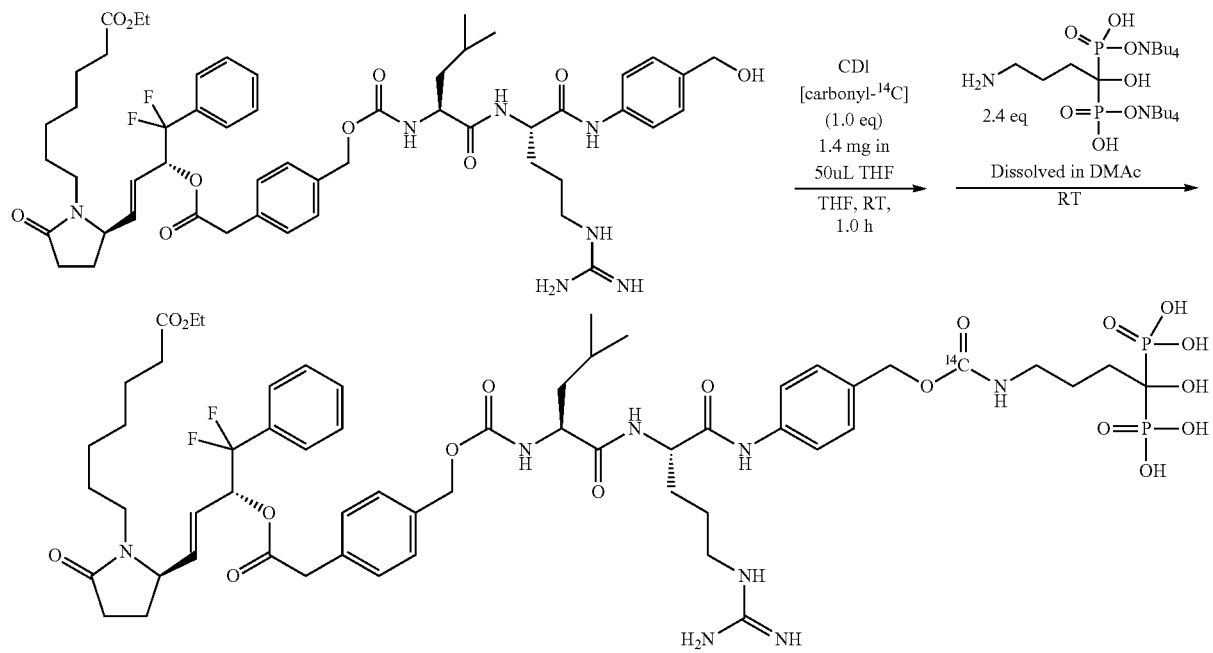

other organs was measured by balance. FIG. 6 shows the results in bone. Table 3 and FIGS. 7A-E show rat organ distribution, uptake and release of a representative conjugate compound 17a.

Dosing of Animals

Female Sprague Dawley rats (Charles River) were about 13 weeks old when received. They were acclimatized to the facility and operators, and were randomly divided to five groups: 6 hour, 1-, 7, 14 and -28 day. Dose: [$^3$H]-17a: 8.90 μCi/rat, [$^{14}$C]-17a 1.77 uCi/rat, and 17a 5.0 mg/kg. Formulation: conjugate 17a was suspended in Poloxamer 188 solution 10%, and adjusted to pH 8.0 by NaHCO$_3$, then diluted by equal volume of PBS. The dosing was done with a fixed volume of 500 μL. The bolus injection and blood sampling were done via the tail vein. Dosed animals showed no unusual behavior or reaction to the drug treatment. Long bones were harvested and counted.

Analysis of the Blood Samples

Three Female Sprague Dawley rats (Charles River) were about 23 weeks old when received. They were acclimatized to the facility and operators. Dose: [$^3$H]-17a: 31.0 μCi/rat. Blood samples (0.5 mL per time point per rat) were taken from the 6-hour group of rats 0.5, 1, 2, 4, 6 hour and placed in heparinized micro-centrifuge tubes. Blood samples from the (500 μL) were centrifuged at ~5000×G until plasma had

TABLE 3

| Percentage of dose | | 6-hour | 1-day | 7-day | 14-day | 28-day |
|---|---|---|---|---|---|---|
| Bone | $^3$H | 2.10 | 2.12 | 1.30 | 0.80 | 0.74 |
|  | $^{14}$C | 5.52 | 4.63 | 3.51 | 2.52 | 2.44 |
| Liver | $^3$H | 8.95 | 2.33 | 0.48 | 0.30 | 0.08 |
|  | $^{14}$C | 7.03 | 2.50 | 0.61 | 0.27 | 0.10 |
| Spleen | $^3$H | 0.35 | 0.22 | 0.076 | 0.039 | 0.037 |
|  | $^{14}$C | 0.34 | 0.23 | 0.086 | 0.050 | 0.039 |
| Kidney | $^3$H | 0.21 | 0.11 | 0.053 | 0.026 | 0.017 |
|  | $^{14}$C | 0.11 | 0.047 | 0.020 | 0.013 | 0.0092 |
| Heart | $^3$H | 0.025 | 0.021 | 0.014 | LOD | LOD |
|  | $^{14}$C | 0.017 | 0.009 | LOD | LOD | LOD |
| Brain | $^3$H | 0.022 | 0.025 | LOD | LOD | LOD |
|  | $^{14}$C | 0.014 | 0.012 | LOD | LOD | LOD |

The results indicated that representative conjugate compound 17a exhibited rapid clearance from circulating blood ($t_{1/2}$ ~0.5 h). Uptake was observed at ~5% by $^{14}$C and 2% by $^3$H, with a release half-life of 4-5 days. The most radio-activity was observed in liver and bones at 6 hours. By 7 days only bones had a significant amount of radio-activity.

The present invention has been described with regard to one or more embodiments. However, it will be apparent to persons skilled in the art that a number of variations and modifications can be made without departing from the scope of the invention as defined in the claims.

All citations are hereby incorporated by reference.

What is claimed is:

1. A compound according to Formula II or a pharmaceutically acceptable salt thereof:

FORMULA II wherein:
X is —CH$_2$—, —S—, —O—, or —NH—;
Y is optionally substituted tetrazole, —C(O)OR', or —C(O)NHSO$_2$V;
R' is H or lower alkyl;
V is optionally substituted lower alkyl, optionally substituted aryl or optionally substituted heteroalkyl;
Z is H or OH;
n is 1, 2 or 3;
m is 0, 1, 2, 3, 4, 5, or 6;
q is 0, 1, 2 or 3;
R$_1$ is each independently —H or halo, or lower alkyl;
Ar is aryl or substituted aryl; and
R$_2$ and R$_3$ are each independently radicals selected from the radicals of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine or valine.

2. The compound of claim 1 wherein R$_2$ is the radical of isoleucine, leucine, phenylalanine, or proline.

3. The compound of claim 1 wherein R$_3$ is the radical of arginine.

4. The compound of claim 1 wherein the compound is (4-((((4-((S)-2-((S)-2-((((4-(2-(((R,E)-4-((R)-1-(7-ethoxy-7-oxoheptyl)-5-oxopyrrolidin-2-yl)-1,1-difluoro-1-phenyl-but-3-en-2-yl)oxy)-2-oxoethyl)benzyl)oxy)carbonyl)amino)-4-methylpentanamido)-5-guanidinopentanamido)benzyl)oxy)carbonyl)amino)-1-hydroxybutane-1,1-diyl)bis(phosphonic acid) or (4-((((4-((S)-2-((S)-2-((((4-(2-(((R,E)-4-((R)-1-(7-ethoxy-7-oxoheptyl)-5-oxopyrrolidin-2-yl)-1,1-difluoro-1-(4-iodophenyl)but-3-en-2-yl)oxy)-2-oxoethyl)benzyl)oxy)carbonyl)amino)-4-methylpentanamido)-5-guanidinopentanamido)benzyl)oxy)carbonyl)amino)-1-hydroxybutane-1,1-diyl)bis(phosphonic acid).

5. A composition comprising the compound of claim 1 in combination with a carrier.

6. The composition of claim 5 wherein the carrier is a pharmaceutically acceptable carrier.

7. A method of selectively delivering the compound of claim 1 or a salt thereof to a bone or an associated site, the method comprising administering the compound of claim 1 or a pharmaceutically acceptable salt thereof to a subject in need thereof.

8. The method of claim 7, wherein the associated site comprises a site adjacent to the bone.

9. The method of claim 7 wherein the bone in need of treatment is a green stick fracture, a compound fracture, a lateral fracture, a pathologic fracture resulting from an invasive tumor, a compression fracture, or a fracture requiring a surgical procedure for realignment of a bone.

10. The method of claim 7 wherein the compound is (4-((((4-((S)-2-((S)-2-((((4-(2-(((R,E)-4-((R)-1-(7-ethoxy-7-oxoheptyl)-5-oxopyrrolidin-2-yl)-1,1-difluoro-1-phenyl-but-3-en-2-yl)oxy)-2-oxoethyl)benzyl)oxy)carbonyl)amino)-4-methylpentanamido)-5-guanidinopentanamido)benzyl)oxy)carbonyl)amino)-1-hydroxybutane-1,1-diyl)bis(phosphonic acid) or (4-((((4-((S)-2-((S)-2-((((4-(2-(((R,E)-4-((R)-1-(7-ethoxy-7-oxoheptyl)-5-oxopyrrolidin-2-yl)-1,1-difluoro-1-(4-iodophenyl)but-3-en-2-yl)oxy)-2-oxoethyl)benzyl)oxy)carbonyl)amino)-4-methylpentanamido)-5-guanidinopentanamido)benzyl)oxy)carbonyl)amino)-1-hydroxybutane-1,1-diyl)bis(phosphonic acid).

11. The method of claim 7, wherein the subject is a human.

12. A method of treating a condition associated with excessive bone loss comprising administering an effective amount of the compound of claim 1 or a pharmaceutically acceptable salt thereof to a subject in need thereof.

13. The method of claim 12, wherein the condition is osteoporosis, Paget's disease, abnormally increased bone turnover, bone graft, periodontal disease, alveolar bone loss, tooth loss, bone fracture, periprostheticosteolysis, osteogenesis imperfecta, or metastatic bone disease.

14. The method of claim 13, wherein the osteoporosis is glucocorticoid-induced osteoporosis.

15. The method of claim 12, wherein the compound is (4-((((4-((S)-2-((S)-2-((((4-(2-(((R,E)-4-((R)-1-(7-ethoxy-7-oxoheptyl)-5-oxopyrrolidin-2-yl)-1,1-difluoro-1-phenyl-but-3-en-2-yl)oxy)-2-oxoethyl)benzyl)oxy)carbonyl)amino)-4-methylpentanamido)-5-guanidinopentanamido)benzyl)oxy)carbonyl)amino)-1-hydroxybutane-1,1-diyl)bis(phosphonic acid) or (4-((((4-((S)-2-((S)-2-((((4-(2-(((R,E)-4-((R)-1-(7-ethoxy-7-oxoheptyl)-5-oxopyrrolidin-2-yl)-1,1-difluoro-1-(4-iodophenyl)but-3-en-2-yl)oxy)-2-oxoethyl)benzyl)oxy)carbonyl)amino)-4-methylpentanamido)-5-guanidinopentanamido)benzyl)oxy)carbonyl)amino)-1-hydroxybutane-1,1-diyl)bis(phosphonic acid).

16. The method of claim 12, wherein the subject is a human.

17. The method of claim 7 wherein the compound stimulates bone growth or inhibits bone resorption.

* * * * *